(12) United States Patent
Keasling et al.

(10) Patent No.: US 7,888,095 B2
(45) Date of Patent: Feb. 15, 2011

(54) METHODS OF GENERATING PROTEIN VARIANTS WITH ALTERED FUNCTION

(75) Inventors: Jay D. Keasling, Berkeley, CA (US); Yasuo Yoshikuni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 62 days.

(21) Appl. No.: 11/915,979

(22) PCT Filed: Jun. 1, 2006

(86) PCT No.: PCT/US2006/021560
§ 371 (c)(1), (2), (4) Date: Jun. 24, 2009

(87) PCT Pub. No.: WO2006/133013
PCT Pub. Date: Dec. 14, 2006

(65) Prior Publication Data
US 2009/0263875 A1    Oct. 22, 2009

Related U.S. Application Data

(60) Provisional application No. 60/687,390, filed on Jun. 3, 2005.

(51) Int. Cl.
*C12N 9/88* (2006.01)
(52) U.S. Cl. .................................................. 435/232
(58) Field of Classification Search ............... None
See application file for complete search history.

(56) References Cited

U.S. PATENT DOCUMENTS

| | | | |
|---|---|---|---|
| 6,358,709 B1 | 3/2002 | Short et al. | |
| 6,602,986 B1 | 8/2003 | Stemmer et al. | |
| 6,713,281 B2 | 3/2004 | Short et al. | |
| 7,172,886 B2 | 2/2007 | Keasling et al. | |
| 7,192,751 B2 | 3/2007 | Keasling et al. | |

OTHER PUBLICATIONS

Caruthers et al. (2000) "Crystal Structure Determination of Aristolochene Synthase from the Blue Cheese Mold, Penicillium roqueforti" *Journal of Biological Chemistry* 275:25533-25539.
Lesburg et al. (1997) "Crystal Structure of Pentalenene synthase: Mechnistic Insights on Terpenoid Cyclization Reactions in Biology"*Science* 277:1820-1824.
Little and Croteau (2002) "Alteration of product formation by directed mutagensis and truncation of the multiple-product sesquiterpene synthases δ-selinene synthase and Y-synthase humulen" *Archives of Biochemistry and Biophysics* 402:120-135.
Martin et al. (2003) "Engineering a mevalonate pathway in *Escherichia coli* for production of terpenoids" *Nature Biotechnology* 21(7):796-802.
Rynkiewicz et al. (2001) "Structure of trichodiene synthase from *Fusarium sporotrichioides* provides mechanistic inferences on the terpene cyclization cascade" *Proc. Natl. Acad. Sci. USA* 98:13543-13548.
Starks et al. (1997) "Structural Basis for Cyclic Terpene Biosynthesis by Tobacco 5-EPi-Aristolochene Synthase" *Science* 277:1815-1820.
Steele et al. (1998) Sesquiterpene Synthases from Grand Fir (*Abies grandis*) *Journal of Biological Chemistry* 273:2078-2089.

*Primary Examiner*—Nashaat T Nashed
(74) *Attorney, Agent, or Firm*—Paula A. Borden; Bozicevic, Field & Francis LLP

(57) ABSTRACT

The present invention provides methods of designing and generating polypeptide variants that have altered function compared to a parent polypeptide. The present invention further provides a computer program product for carrying out the design of a variant polypeptide. The present invention further provides nucleic acids encoding terpene cyclase variants, as well as vectors and host cells comprising the nucleic acids. The present invention further provides variant terpene cyclases; methods of producing the variant terpene cyclases; and methods of producing isoprenoid compounds.

2 Claims, 18 Drawing Sheets

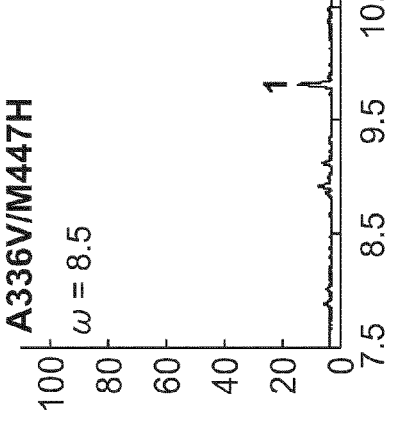
FIG. 8C
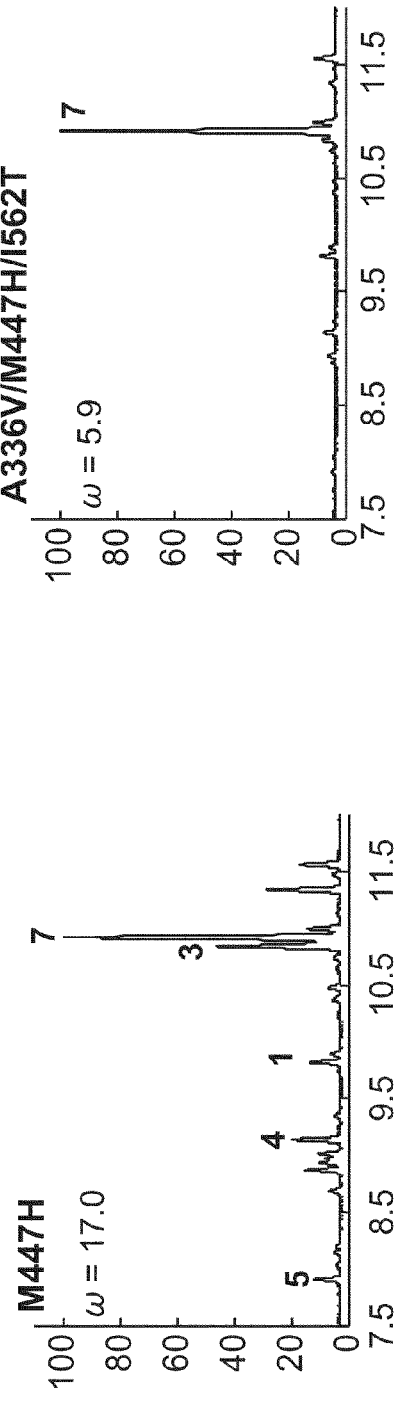
FIG. 8D
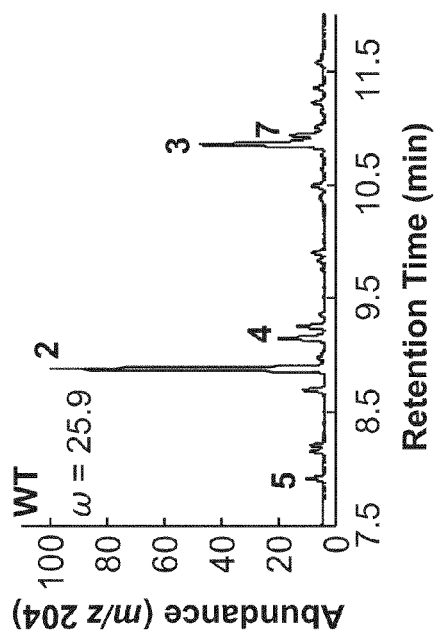
FIG. 8A
FIG. 8B

Nucleotide sequence of designed γ-humulene synthase-
ATGGCTCAAATCAGCGAATCAGTGTCTCCAAGCACCGACCTTAAAAGCACGGAATC
TTCTATTACCAGCAACCGCCACGGTAACATGTGGGAAGATGACCGCATTCAGAGCT
TAAACAGCCCATATGGCGCACCCGCTTATCAGGAACGTAGCGAAAAATTGATTGAA
GAAATTAAGCTCCTGTTTCTGTCCGATATGGACGATAGTTGCAATGATTCGGATCGC
GACTTGATCAAACGCCTGGAGATCGTAGATACGGTTGAGTGTCTGGGCATTGATCG
TCATTTCCAACCTGAAATTAAGCTGGCGCTGGATTACGTGTACCGTTGCTGGAATG
AGCGTGGCATCGGAGAAGGTAGCCGTGATAGCTTAAAAAAGGACCTGAATGCGAC
CGCCTTGGGCTTTCGGGCTTTACGCTTACACCGTTATAATGTAAGCTCAGGAGTGC
TGGAGAACTTCCGTGATGACAATGGTCAATTCTTTTGCGGTTCTACTGTGGAGGAG
GAAGGCGCGGAGGCCTACAATAAACATGTACGTTGCATGCTGTCCCTGTCCCGCGC
TTCCAATATTTTATTCCCGGGCGAGAAAGTGATGGAAGAAGCGAAGGCGTTTACGA
CCAACTATCTTAAGAAAGTCCTGGCGGGTCGTGAAGCAACTCATGTCGACGAGAGT
CTCCTTGGAGAGGTCAAGTATGCACTAGAATTTCGTGGCATTGTTCCGTGCAGCG
CTGGGAGGCACGTTCTTTTATCGAAATTTTCGGTCAGATTGATAGTGAACTGAAAA
GCAACCTCTCTAAAAAAATGCTCGAACTCGCAAAACTTGATTTTAACATACTCCAGT
GTACGCATCAAAAAGAGCTCCAGATCATTAGTCGATGGTTCGCCGATTCAAGTATC
GCAAGTCTGAACTTTTACCGTAAATGCTATGTGGAATTTTACTTCTGGATGGCCGCG
GCAATTTCAGAACCAGAATTTAGTGGCTCTCGCGTGGCATTCACTAAAATTGCGAT
CTTGATGACAATGTTAGATGACTTATACGACACGCATGGGACGCTGGATCAATTGA
AAATATTTACCGAAGGTGTGCGCAGGTGGGACGTGTCGCTGGTGGAGGGCCTGCC
GGATTTCATGAAAATTGCCTTTGAGTTCTGGTTAAAGACCTCCAACGAACTGATTG
CGGAGGCGGTTAAGGCCCAAGGCCAGGATATGGCGGCCTATATCCGCAAAAACGC
TTGGGAACGCTATCTGGAAGCGTATTTGCAGGATGCCGAATGGATCGCCACCGGTC
ACGTTCCGACATTCGATGAATATCTGAACAATGGCACCCCCAACACCGGTATGTGT
GTACTTAATCTGATCCCGTTGCTGCTTATGGGCGAACACTTGCCGATCGATATTCTT
GAACAGATCTTTCTGCCGAGCCGGTTCCACCATCTGATTGAACTGGCTAGCCGACT
GGTCGATGATGCGAGAGATTTTCAAGCCGAAAAGATCATGGTGATTTATCCTGCA
TCGAATGCTACCTGAAAGACCATCCGGAATCAACAGTTGAAGACGCCCTGAATCAC
GTCAACGGCCTGCTGGGGAATTGTTTGCTGGAAATGAATTGGAAATTTCTGAAAAA
ACAGGACTCGGTACCTCTGTCGTGTAAAAAATACTCATTCCACGTCCTGGCGCGGT
CGATTCAGTTTATGTATAACCAGGGGACGGGTTTTCGATTTCGAACAAAGTTATTA
AAGACCAGGTCCAGAAAGTTCTAATCGTTCCGGTTCCTATATAA (SEQ ID NO:45)

FIG. 10

Wild type humulene cyclase amino acid sequence
MAQISESVSPSTDLKSTESSITSNRHGNMWEDDRIQSLNSPYGAPAYQERSEKLIEEIK
LLFLSDMDDSCNDSDRDLIKRLEIVDTVECLGIDRHFQPEIKLALDYVYRCWNERGIG
EGSRDSLKKDLNATALGFRALRLHRYNVSSGVLENFRDDNGQFFCGSTVEEEGAEAY
NKHVRCMLSLSRASNILFPGEKVMEEAKAFTNYLKKVLAGREATHVDESLLGEVKY
ALEFPWHCSVQRWEARSFIEIFGQIDSELKSNLSKKMLELAKLDFNILQCTHQKELQI
ISRWFADSSIASLNFYRKCYVEFYFWMAAAISEPEFSGSRVAFTKIAILMTMLDDLYDT
HGTLDQLKIFTEGVRRWDVSLVEGLPDFMKIAFEFWLKTSNELIAEAVKAQGQDMAA
YIRKNAWERYLEAYLQDAEWIATGHVPTFDEYLNNGTPNTGMCVLNLIPLLLMGEHL
PIDILEQIFLPSRFHHLIELASRLVDDARDFQAEKDHGDLSCIECYLKDHPESTVEDAL
NHVNGLLGNCLLEMNWKFLKKQDSVPLSCKKYSFHVLARSIQFMYNQGDGFSISNK
VIKDQVQKVLIVPVPI (SEQ ID NO:46)

FIG. 11

*E*-β-bisabolenesynthase (BBA)

MAQISESVSPSTDLKSTESSITSNRHGNMWEDDRIQSLNSPYGAPAYQERSEKLIEEI

KLLFLSDMDDSCNDSDRDLIKRLEIVDTVECLGIDRHFQPEIKLALDYVYRCWNER

GIGEGSRDSLKKDLNATALGFRALRLHRYNVSSGVLENFRDDNGQFFCGSTVEEG

AEAYNKHVRCMLSLSRASNILFPGEKVMEEAKAFTTNYLKKVLAGREATHVDESLL

GEVKYALEFPWHCSVQRWEARSFIEFGQIDSELKSNLSKKMLELAKLDENILQCTH

QKELQIISRWFADSSIASLNFYRKCYVEFYFWMAAAISEPEFSGSRVAFTKIVLMTM

LDDLYDTHGTLDQLKIFTEGVRRWDVSLVEGLPDFMKIAFEFWLKTSNELIAEAVKA

QGQDMAAYIRKNAWERYLEAYLQDAEWLATGHVPTFDEYLNNGTPNTGHCVLNLIP

LLLMGEHLPIDILEQIFLPSRFHHLIELASRLVDDARDFQAEKDHGDLSCIECYLKD

HPESTVEDALNHVNGLLGNCLLEMNWKFLKKQDSVPLSCKKYSFHVLARSTQFMY

NQGDGFSISNKVIKDQVQKVLIVPVPI (SEQ ID NO:47)

FIG. 12

*E*-β-farnesene/*Z,E*-α-farnesene synthase (BFN)

MAQISESVSPSTDLKSTESSITSNRHGNMWEDDRIQSLNSPYGAPAYQERSEKLIEEI
KLLFLSDMDDSCNDSDRDLIKRLEIVDTVECLGIDRHFQPEIKLALDYVYRCWNER
GIGEGSRDSLKKDLNATALGFRALRLHRYNVSSGVLENFRDDNGQFFCGSTVEEG
AEAYNKHVRCMLSLSRASNILFPGEKVMEEAKAFTTNYLKKVLAGREATHVDESLL
GEVKYALEFPWHCSVQRWEARSFIEIFGQIDSELKSNLSKKMLELAKLDFNILQCTH
QKELQIISRWFEADSSIASLNFYRKCYVEFYFPMAAAISEPEFSGSRVAFTKIAILMTML
DDLYDTHGTLDQLKIFTEGVRRWDVSLVEGLPDFMKIAFEFWLKTSNELIAEAVKA
QGQDMAAYIRKNAWERYLEAYLQDAEWIATGHVPTFDEYLNNGTPNTGMCVLNLIP
LLLMGEHLPIDILEQIFLPSRFHHLIELASRLVDDARDFQAEKDHGDLSCIECYLKD
HPESTVEDALNHVNGLLGNCLLEMNWKFLKKQDSVPLSCKKYSFHVLARSIQFMY
NQGDGFSISNKVIKDQVQKVLIVPVPI (SEQ ID NO:48)

FIG. 13

Sibirene cyclase (SIB)

MAQISESVSPSTDLKSTESSITSNRHGNMWEDDRIQSLNSPYGAPAYQERSEKLIEEI
KLLFLSDMDDSCNDSDRDLIKRLEIVDTVECLGIDRHFQPEIKLALDYVYRCWNER
GIGEGSRDSLKKDLNATALGFRALRLHRYNVSSGVLENFRDDNGQFFCGSTVEEEG
AEAYNKHVRCMLSLSRASNILFPGEKVMEEAKAFTTNYLKKVLAGREATHVDESLL
GEVKYALEFPWHCSVQRWEARSFIEIFGQIDSELKSNLSKKMLELAKLDFNILQCTH
QKELQIISRWFADSSIASLNFYRKCYVEQYFWMAAAISEPEFSGSRVAFTKIAILATM
LDDLYDTHGTLDQLKIFTEGVRRWDVSLVEGLPDFMKIAFEFWLKTSNELIAEAVKA
QGQDMAAYIRKNAWERYLEAYLQDAEWIATGHVPTFDEYLNNGTPNTGFCVLNLIP
LLLMGEHLPIDILEQIFLPSRFHHLIELASRLVDDARDFQAEKDHGDLSCIECYLKD
HPESTVEDALNHVNGLLGNCLLEMNWKFLKKQDSVPLSCKKYSFHVLARSIQFMY
NQGDGFSISNKVIKDQVQKVLIVPVPI (SEQ ID NO:49)

FIG. 14

γ-humulene synthase (HUM)

MAQISESVSPSTDLKSTESSITSNRHGNMWEDDRIQSLNSPYGAPAYQERSEKLIEEI

KLLFLSDMDDSCNDSDRDLIKRLEIVDTVECLGIDRHFQPEIKLALDYVYRCWNER

GIGEGSRDSLKKDLNATALGFRALRLHRYNVSSGVLENFRDDNGQFFCGSTVEEEG

AEAYNKHVRCMLSLSRASNILFPGEKVMEEAKAFTTNYLKKVLAGREATHVDESLL

GEVKYALEFPWHCSVQRWEARSFIEIFGQIDSELKSNLSKKMLELAKLDFNILQCTH

QKELQIISRWFADSSIASLNFYRKCYVEFYFWMAAAISEPEFSGSRVAFTKIAILNTM

LDDLYDTHGTLDQLKIFTEGVRRWDVSLVEGLPDFMKIAFEFWLKTSNELIAEAVKA

QGQDMAAYIRKNAWERYLEAYLQDAEWIATGHVPTFDEYLNNGTPNTGMCVLNLIP

LLLMGEHLPIDILEQIFLPSRFHHLIELACRLVDDARDFQAEKDHGDLSCIECYLKD

HPESTVEDALNHVNGLLGNCLLEMNWKFLKKQDSVPLSCKKYSFHVLARSIQFIYN

QGDGFSISNKVIKDQVQKVLIVPVPI (SEQ ID NO:50)

FIG. 15

Longifolene cyclase (LFN)

MAQISESVSPSTDLKSTESSITSNRHGNMWEDDRIQSLNSPYGAPAYQERSEKLIEEI
KLLFLSDMDDSCNDSDRDLIKRLEIVDTVECLGIDRHFQPEIKLALDYVYRCWNER
GIGEGSRDSLKKDLNATALGFRALRLHRYNVSSGVLENFRDDNGQFFCGSTVEEEG
AEAYNKHVRCMLSLSRASNILFPGEKVMEEAKAFTTNYLKKVLAGREATHVDESLL
GEVKYALEFPWHCSVQRWEARSFIEIFGQIDSELKSNLSKKMLELAKLDFNILQCTH
QKELQIISRWFADSSIASLNFYRKCYVEFYFWMNAAISEPEFSGSRVAFTKISILMTM
LDDLYDTHGTLDQLKIFTEGVRRWDVSLVEGLPDFMKIAFEFWLKTSNELIAEAVKA
QGQDMAAYIRKNAWERYLEAYLQDAEWLATGHVPTFDEYLNNGTPNTGMCVLNLIP
LLLMGEHLPIDILEQIFLPSRFHHLIELACRLVDDARDFQAEKDHGDLSCIECYLKD
HPESTVEDALNHVNGLLGNCLLEMNWKFLKKQDSVPLSCKKYSFHVLARSVQFMY
NQGDGFSISNKVIKDQVQKVLIVPVPI (SEQ ID NO:51)

FIG. 16

α-longipinene synthase (ALP)

MAQISESVSPSTDLKSTESSITSNRHGNMWEDDRIQSLNSPYGAPAYQERSEKLIEEI

KLLFLSDMDDSCNDSDRDLIKRLEIVDTVECLGIDRHFQPEIKLALDYVYRCWNER

GIGEGSRDSLKKDLNATALGFRALRLHRYNVSSGVLENFRDDNGQFFCGSTVEEG

AEAYNKHVRCMLSLSRASNILFPGEKVMEEAKAFTTNYLKKVLAGREATHVDESLL

GEVKYALEFPWHCSVQRWEARSFIEIFGQIDSELKSNLSKKMLELAKLDFNILQCTH

QKELQIISRWFADSSIASLNFYRKCYVEFYFWMAAAISEPEFSGSRVAFTKICILMTM

LDDLYDTHGTLDQLKIFTEGVRRWDVSLVEGLPDFMKIAFEFWLKTSNELIAEAVKA

QGQDMAAYIRKNAWERYLEAYLQDAEWIATGHVPTFDEYLNNGTPNCGMCVLNLI

PLLLMGEHLPIDILEQIFLPSRFHHLIELACRLVDDARDFQAEKDHGDLSCIECYLKD

HPESTVEDALNHVNGLLGNCLLEMNWKFLKKQDSVPLSCKKYSFHVLARSLQFLY

NQGDGFSISNKVIKDQVQKVLIVPVPI (SEQ ID NO:52)

FIG. 17

α-ylangene (AYG)

MAQISESVSPSTDLKSTESSITSNRHGNMWEDDRIQSLNSPYGAPAYQERSEKLIEEI
KLLFLSDMDDSCNDSDRDLIKRLEIVDTVECLGIDRHFQPEIKLALDYVYRCWNER
GIGEGSRDSLKKDLNATALGFRALRLHRYNVSSGVLENFRDDNGQFFCGSTVEEG
AEAYNKHVRCMLSLSRASNILFPGEKVMEEAKAFTTNYLKKVLAGREATHVDESLL
GEVKYALEFPWHCSVQRWEARSFIEIFGQIDSELKSNLSKKMLELAKLDFNILQCTH
QKELQIISRWFADSSIASLNFYRKCYVEFYFWMAAAISEPEFSGSRVAFTKIAILMTM
LDDLYDTHGTLDQLKIFTEGVRRWDVSLVEGLPDFMKIAFEFWLKTSNELIAEAVKA
QGQDMAAYIRKNAWERYLEAYLQDAEWIATGHVPTFDEYLNNGTPNTGMCVLNLIP
LLLMGEHLPIDILEQIFLPSRFHHLIELAARLVDDARDFQAEKDHGDLSCIECYLKD
HPESTVEDALNHVNGLLGNCLLEMNWKFLKKQDSVPLSCKKYSFHVLARSIQFMF
NQGDFSISNKVIKDQVQ

US 7,888,095 B2

METHODS OF GENERATING PROTEIN VARIANTS WITH ALTERED FUNCTION

STATEMENT REGARDING FEDERALLY SPONSORED RESEARCH

The U.S. government may have certain rights in this invention, pursuant to grant no. 2001-52104-1128 awarded by the U.S. Department of Agriculture.

CROSS REFERENCE TO RELATED APPLICATIONS

This application is a national stage filing under 35 U.S.C. §371 of International Patent Application Serial No. PCT/US2006/021560, which was filed on Jun. 1, 2006 and which was published in English under PCT Article 21(2) as WO 2006/133013 on Dec. 14, 2006, which International Patent Application claims benefit of priority of U.S. Provisional Patent Application No. 60/687,390, filed Jun. 3, 2005, which application is incorporated herein by reference in its entirety.

FIELD OF THE INVENTION

The present invention is in the field of protein engineering, and in particular method of designing and generating protein variants having altered function, using rational design.

BACKGROUND OF THE INVENTION

Directed evolution, modifying a parent protein such that the modified protein exhibits a desirable property, can be achieved by mutagenizing one or more parent proteins and screening the mutants to identify those having a desired property. A variety of directed evolution methods are currently available for generating protein variants that exhibit altered function, compared to a parent polypeptide. However, currently available methods involve generation of tens of thousands to a million or more mutants, which must be screened to find a few critical mutations. Thus, application of currently available methods is limited by inefficiency of screening the enormous number of mutants that are generated.

There is a need in the art for efficient methods of designing and generating protein variants that exhibit altered function, without the need for generating and screening large numbers of variants.

Literature

Lesburg et al. (1997) *Science* 277:1820-1824; Starks et al. (1997) *Science* 277:1815-1820; Caruthers et al. (2000) *J. Biol. Chem.* 275:25533-25539; Rynkiewicz et al. (2001) *Proc. Natl. Acad. Sci. USA* 98:13543-13548; Steele et al. (1998) *J. Biol. Chem.* 273:2078-2089; and Little and Croteau (2002) *Arch. Biochem. Biophys.* 402:120-135; U.S. Pat. Nos. 6,358,709, 6,713,281, and 6,602,986; U.S. Patent Publication No. 2004/005678; U.S. Patent Publication No. 2003/0148479; Martin et al. (2003) *Nat. Biotech.* 21(7):796-802.

SUMMARY OF THE INVENTION

The present invention provides methods of designing and generating polypeptide variants that have altered function compared to a parent polypeptide. The present invention further provides a computer program product for carrying out the design of a variant polypeptide. The present invention further provides nucleic acids encoding terpene cyclase variants, as well as vectors and host cells comprising the nucleic acids. The present invention further provides variant terpene cyclases; methods of producing the variant terpene cyclases; and methods of producing terpenoid compounds.

BRIEF DESCRIPTION OF THE DRAWINGS

FIGS. 8A-D depict results of analyses of variants.

FIG. 10 depicts a nucleotide sequence (SEQ ID NO:45) encoding a parent γ-humulene cyclase, where the nucleotide sequence is codon optimized for expression in *E. coli*.

FIG. 11 depicts the amino acid sequence (SEQ ID NO:46) of wild-type (parent) γ-humulene cyclase.

FIG. 12 depicts the amino acid sequence (SEQ ID NO:47) of the M447H/A336V/I562T variant, β-bisabolene cyclase (BBA).

FIG. 13 depicts the amino acid sequence (SEQ ID NO:48) of the W315P variant, E-β-farnesene/Z,E-α-farnesene synthase (BFN).

FIG. 14 depicts the amino acid sequence (SEQ ID NO:49) of the F312Q/M339A/M447F variant, sibirene cyclase (SIB).

FIG. 15 depicts the amino acid sequence (SEQ ID NO:50) of the M339N/S484C/M565I variant, γ-humulene cyclase (HUM).

FIG. 16 depicts the amino acid sequence (SEQ ID NO:51) of the A336S/S484C/I562V variant, longifolene cyclase (LFN).

FIG. 17 depicts the amino acid sequence (SEQ ID NO:52) of the A336C/T445C/S484C/I562L/M565L variant, α-longipene cyclase (ALP).

FIG. 18 depicts the amino acid sequence (SEQ ID NO:53) of the S484A/Y566F variant, γ-humulene cyclase (AYG).

DEFINITIONS

Figure 1:
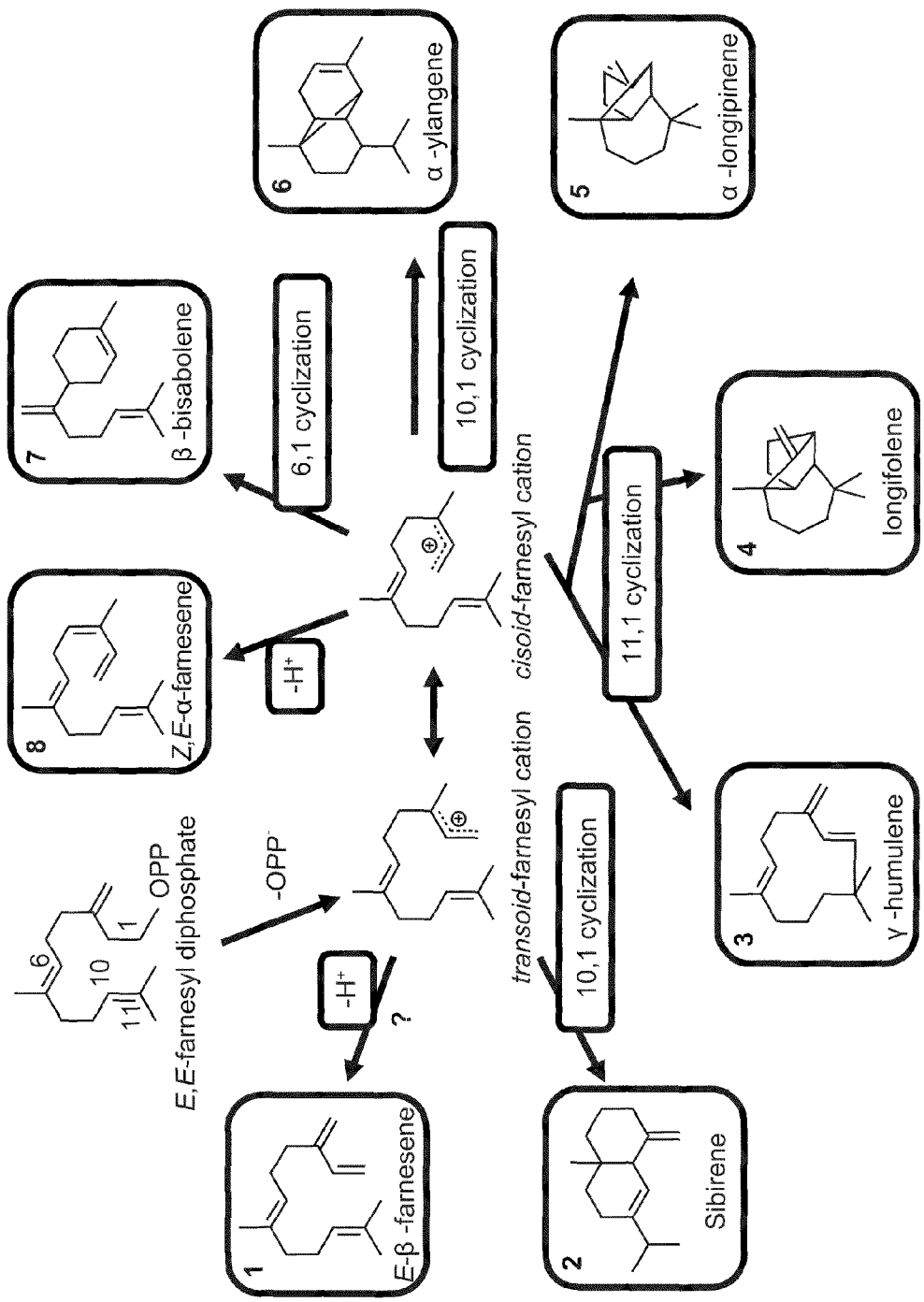
FIG. 1 depicts γ-Humulene cyclase cyclization reaction mechanisms.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, serine-threonine, phenylalanine-tyrosine, lysine-arginine, alanine-valine, aspartate-glutamate, and asparagine-glutamine.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

Expression cassettes may be prepared comprising a transcription initiation or transcriptional control region(s) (e.g., a promoter), the coding region for the protein of interest, and a transcriptional termination region. Transcriptional control regions include those that provide for over-expression of the protein of interest in the genetically modified host cell; those that provide for inducible expression, such that when an inducing agent is added to the culture medium, transcription of the coding region of the protein of interest is induced or increased to a higher level than prior to induction.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, diterpenes, triterpenes, and polyterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate.

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination that will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a terpene cyclase variant" includes a plurality of such variants and reference to "the algorithm" includes reference to one or more algorithms and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of designing and generating polypeptide variants that have altered function compared to a parent polypeptide. The present invention further provides a computer program product for carrying out the design of a variant polypeptide. The present invention further provides nucleic acids encoding terpene cyclase variants, as well as vectors and host cells comprising the nucleic acids. The present invention further provides variant terpene cyclases; and methods of producing the variant terpene cyclases. The present invention further provides methods of producing terpenoid compounds.

Methods of Designing and Generating Polypeptide Variants

The present invention provides methods of designing and generating polypeptide variants that have altered function compared to a parent polypeptide. The methods generally involve: a) providing a library of amino acid sequences for candidate mutant polypeptides having one or more amino acid substitutions (e.g., one amino acid substitution, two amino acid substitutions, three amino acid substitutions, four amino acid substitutions, etc.) as compared to the parent polypeptide, where each member of the library of amino acid sequences is assigned an omega value that has been determined from the empirically observed individual effect of the member's one or more substitutions on the function; and b) selecting at least one candidate from the library of amino acid sequences, based on the at least one candidate's omega value, where the omega value of the at least one selected candidate meets a predetermined threshold (e.g., the omega value of the at least one selected candidate is lower than the omega value of the parent polypeptide), and where the variant polypeptide comprises the candidate amino acid sequence and exhibits altered function as compared to the parent polypeptide.

In some embodiments, the individual effect of the one or more amino acid substitutions on the function is determined using a library of mutant polypeptides, where each member of the library of mutant polypeptides comprises a single amino acid substitution compared to the amino acid sequence of the parent polypeptide. A library of mutant polypeptides, each member of which has a single amino acid substitution compared to a parent polypeptide, is generated using any known method. For example, in some embodiments, a nucleic acid comprising a nucleotide sequence encoding the parent polypeptide is mutated, such that a library of nucleic acids is generated, each member of which library of nucleic acids comprises a nucleotide sequence encoding a polypeptide having a single amino acid substitution compared to the parent polypeptide. Methods for generating such a library of nucleic acids are well known in the art.

The omega value of the selected candidate sequence(s) is generally lower than the omega value of the parent polypeptide. Thus, e.g., the omega value of the selected candidate sequence(s) is generally at least about 5% lower, at least about 10% lower, at least about 15% lower, at least about 20% lower, at least about 25% lower, at least about 30% lower, at least about 35% lower, at least about 40% lower, at least about 45% lower, at least about 50% lower, at least about 55% lower, at least about 60% lower, at least about 65% lower, at least about 70% lower, at least about 75% lower, at least about 80% lower, or more than 80% lower, than the omega value of the parent polypeptide.

Typically, a plurality of amino acids are mutated, such that the library of mutant polypeptides, each comprising a single amino acid substitution compared to a parent polypeptide, provides a plurality of amino acid substitutions in a plurality of amino acid residues. In some embodiments, each amino acid that is substituted is individually substituted by from about 1 amino acid to about 19 different amino acids, e.g., from about 1 amino acid to about 5 different amino acids, from about 5 different amino acids to about 10 different amino acids, from about 10 different amino acids to about 15 different amino acids, or from about 15 different amino acids to about 19 different amino acids.

Using a subject method, polypeptide variants can be generated based on a wide variety of parent polypeptides, where parent polypeptides include, but are not limited to, enzymes, antibodies, transcription factors, receptors for ligands, polypeptide ligands for receptors, signal proteins, a fluorescent protein, a carrier protein, a small molecule binding protein, a large molecule binding protein, and the like. A "parent" polypeptide is any polypeptide that serves as a reference for generating a variant polypeptide, where a variant polypeptide comprises one or more amino acid substitutions compared to the amino acid sequence of the parent polypeptide. A "parent" polypeptide is in some embodiments a wild-type polypeptide, e.g., a polypeptide found in nature.

In some embodiments, the parent polypeptide is an enzyme; and the variant enzyme exhibits an altered product profile, compared to the parent enzyme. In some embodiments, the parent enzyme is an enzyme that, upon action on a single substrate, yields a plurality of (e.g., two or more, three or more, four or more, five or more, six or more, seven or more, eight or more, etc.) different products. In some embodiments, where the parent polypeptide is an enzyme that yields three or more different products upon catalytic action upon a single substrate, the variant enzyme is one that, upon catalytic action on the substrate, will preferentially yield two products from among the three or more products. For example, in some embodiments, the proportion of two products from among the three or more products is at least about 30%, at least about 40%, at least about 50%, at least about 60%, at least about 70%, at least about 80%, at least about 90%, at least about 95%, at least about 98%, at least about 99%, or more than about 99%, of the total yield of the three or more products. In some embodiments, where the parent polypeptide is an enzyme that yields a plurality of different products upon catalytic action upon a single substrate, the variant enzyme is one that, upon catalytic action on the substrate, will preferentially yield a single product from among the plurality of products. For example, in some embodiments, the proportion of the single product is at least about 30%, at least about 40%, at least about 50%, at least about 60%, at least about 70%, at least about 80%, at least about 90%, at least about 95%, at least about 98%, at least about 99%, or more than about 99%, of the total yield of the plurality of products.

In some embodiments, where the parent polypeptide is an enzyme that yields at least a first product upon catalytic action on a substrate, the variant polypeptide yields a second product upon catalytic action on the substrate, where the second product is different from the first product. In other words, the variant polypeptide yields a product that the parent polypeptide does not yield. In many of these embodiments, the variant polypeptide preferentially yields the second product, e.g., the proportion of the second product yielded by the variant enzyme is at least about 30%, at least about 40%, at least about 50%, at least about 60%, at least about 70%, at least about 80%, at least about 90%, at least about 95%, at least about 98%, at least about 99%, or more than about 99%, of the total yield of products by the variant enzyme.

In some embodiments, the parent polypeptide is an enzyme that yields a single product upon catalytic action on any of a plurality of substrates; and the variant enzyme exhibits altered substrate specificity. In some embodiments, where the parent polypeptide is an enzyme that yields a single product upon catalytic action upon any of a plurality of different substrates, the variant enzyme is one that will yield the single product by preferentially modifying a single substrate from among the plurality of substrates. For example, in some embodiments, the single product is produced by catalytic action of the variant enzyme preferentially on one substrate from among the plurality of substrates.

One non-limiting example of an enzyme that yields a single product upon catalytic action on any of a plurality of substrates is paraoxonase. Paraoxonase catalyzes an enzymatic reaction, using substrates such as phenyl acetate, DepCyc, Fast Red, paraoxon; where the enzymatic reaction is hydrolysis of an ester bond (e.g., ester, thioester, and phosphester). See, e.g., Aharoni et al. (2004) Proc. Natl. Acad. Sci. USA 101:482-487; and Aharoni et al. (2005) Nature Genetics 37:73-76.

In some embodiments, the parent polypeptide is an enzyme that produces a plurality of products from any of a plurality of substrates; and the variant enzyme is one that exhibits both altered substrate specificity and an altered product profile, compared to the parent enzyme. In some embodiments, where the parent polypeptide is an enzyme that yields a plurality of (e.g., two or more, three or more, four or more, five or more, six or more, seven or more, eight or more, etc.) different products upon catalytic action upon any of a plurality of different substrates. In some embodiments, where the parent polypeptide is an enzyme that yields three or more different products upon catalytic action upon any of a plurality of different substrates, the variant enzyme is one that, upon catalytic action preferentially on one substrate from among the plurality of substrates, will preferentially yield two products from among the three or more products. For example, in some embodiments, the proportion of two products from among the three or more products is at least about 30%, at least about 40%, at least about 50%, at least about 60%, at least about 70%, at least about 80%, at least about 90%, at least about 95%, at least about 98%, at least about 99%, or more than about 99%, of the total yield of the three or more products. In some embodiments, where the parent polypeptide is an enzyme that yields a plurality of different products upon catalytic action upon any of a plurality of different substrates, the variant enzyme is one that, upon catalytic action preferentially on one substrate from among the plurality of substrates, will preferentially yield a single product from among the plurality of products. For example, in some embodiments, the proportion of the single product is at least about 30%, at least about 40%, at least about 50%, at least about 60%, at least about 70%, at least about 80%, at least about 90%, at least about 95%, at least about 98%, at least about 99%, or more than about 99%, of the total yield of the plurality of products.

Non-limiting examples of enzymes that produce a plurality of products from any of a plurality of substrates are sesquiterpene synthases. For example, γ-humulene cyclase and δ-selinene cyclase can both use FPP and GPP as substrates, and catalyze synthesis of multiple products from FPP and GPP. See, e.g., Steele et al. (1996) Proc. Natl. Acad. Sci. USA 273:2078-2089.

In some embodiments, the parent polypeptide is an antibody, where "antibody" includes single chain antibodies, monoclonal antibodies, antibody fragments that retain antigen-binding (e.g., Fv, F(ab')$_2$ and Fab fragments), and the like. In some embodiments, the parent antibody binds specifically to a first antigen (or epitope); and the variant antibody binds specifically to a second antigen (or epitope). The term "specific binding," in the context of antibody binding to an antigen, is a term well understood in the art and refers to binding of an antibody to the antigen to which the antibody was raised, but not other, unrelated antigens. Specific binding typically refers to binding with an affinity of at least about $10^{-6}$ M, at least about $10^{-7}$ M, at least about $10^{-8}$ M, or at least about $10^{-9}$ M, or greater.

In some embodiments, the parent polypeptide is a receptor, e.g., a cell surface receptor, a nuclear receptor, a cytoplasmic receptor, etc., that binds to a first ligand; and the variant polypeptide is a receptor that binds to a second ligand. In some embodiments, the parent polypeptide is a receptor that binds to a first ligand and a second ligand; and the variant polypeptide is a receptor that binds preferentially to the first ligand (e.g., binding of the second ligand to the variant polypeptide is reduced (e.g., the affinity of binding for the second ligand is reduced by at least about 20%, at least about 30%, at least about 40%, at least about 50%, at least about 60%, at least about 70%, at least about 80%, at least about 90%, or more); or binding to the second ligand is undetectable).

In some embodiments, the parent polypeptide is a fluorescent protein. Fluorescent proteins are proteins that, following excitation at a first wavelength of light, will emit light at a second wavelength. For example, the excitation spectra of fluorescent proteins typically ranges from about 300 to 700, while the emission spectra of typically ranges from about 400 to 800. Fluorescent proteins are known in the art, and include green fluorescent proteins (GFP) from *Aequoria victoria*; derivatives of GFP that are known in the art; and any of a variety of fluorescent proteins from Anthozoan species, as described in, e.g., Matz et al. (1999) Nature Biotechnol. 17:969-973. In some embodiments, following excitation at an excitation wavelength of light, the parent fluorescent protein emits light at a first emission wavelength, and the variant polypeptide emits light at second emission wavelength.

In some embodiments, the amino acid residues that are substituted are chosen randomly. In some embodiments, e.g., where the parent polypeptide is an enzyme, the amino acid residues that are substituted are in an active site contour of the parent polypeptide. In some embodiments, e.g., where the parent polypeptide is a protein that binds a ligand (e.g., a small molecule; an antigen; a macromolecule, such as a polypeptide, a nucleic acid, a lipid, a polysaccharide, a lipoprotein, a lipopolysaccharide, a glycoprotein, a glycolipid, a glycolipoprotein, etc.), the amino acid residues that are substituted are in the binding site of the polypeptide. In some embodiments, the amino acid residues that are substituted are proximal to the active site or the binding site of the parent polypeptide. In some embodiments, the amino acid residues that are substituted are outside of the active site or the binding site of the parent polypeptide.

In other embodiments, the amino acid residues that are substituted are those that have been identified as contributing to a function of the parent polypeptide. Amino acid residues that contribute to one or more functions of a parent polypeptide are referred to herein as "plasticity residues." In some embodiments, plasticity residues are identified by aligning the amino acid sequence of the parent polypeptide with the amino acid sequence of a second polypeptide that is a member of the same family or superfamily as the parent polypeptide, and wherein the second polypeptide shares at least about 15% amino acid sequence identity with the amino acid sequence of the parent polypeptide, e.g., wherein the second polypeptide shares from about 15% to about 20%, from about 20% to about 25%, from about 25% to about 30%, from about 30% to about 35%, from about 35% to about 40%, from about 40% to about 45%, from about 45% to about 50%, from about 50% to about 60%, or from about 60% to about 70%, or greater than 70%, amino acid sequence identity with the amino acid sequence of the parent polypeptide. In some embodiments, the alignment is carried out by overlaying the amino acid sequence of the parent polypeptide on the x-ray crystallographic structure of the second polypeptide that is in the same family or superfamily as the parent polypeptide. In other embodiments, plasticity residues are identified by analyzing the crystal structure of the parent protein; by homology structural modeling; by directed evolution; and by biochemical studies (e.g., wherein one or more amino acid residues are substituted, and observing the effect of the amino acid substitution(s) on a function of the parent protein).

The omega value is determined from the empirically observed individual effect of the member's one or more substitutions (e.g., a single amino acid substitution; two amino acid substitutions; three amino acid substitutions; four amino acid substitutions; etc.) on the function. A library of mutant polypeptides is screened for the effect of single amino acid substitutions on a function of the mutant polypeptide, compared to the same function in parent polypeptide. The effect of individual (single) amino acid substitutions on any given function is readily determined using any assay that is appropriate to the function.

Functions or properties that may be altered include, but are not limited to, enzymatic activity (where the parent polypeptide and the corresponding variant polypeptide are enzymes), where enzymatic activity includes specific activity, substrate specificity, and product profile (where "product profile" refers to the produce(s) generated using a given substrate); antigen-binding properties (where the parent polypeptide and the corresponding variant polypeptide are antibodies or antigen-binding fragments of antibodies), where antigen-binding properties include antigen specificity, antigen binding affinity, etc.; ligand binding properties (e.g., where the parent polypeptide and the corresponding variant polypeptide are ligand receptors), where ligand binding properties include ligand specificity, ligand affinity, etc.; substrate binding properties, e.g., where the parent polypeptide and the corresponding variant polypeptide are transcription factors, the function being altered is in some embodiments specificity for a particular nucleotide sequence; protein stability; protein solubility; fluorescent properties (e.g., where the parent polypeptide is a fluorescent protein); signal transduction properties (e.g., where the parent polypeptide is a signal transduction protein such as a receptor); binding specificity and/or affinity to a small molecule; binding specificity and/or affinity to a large molecule; and the like.

The omega value for the one or more amino acid substitutions is assigned, based on the effect of the individual amino acid substitutions on a function of the polypeptide. The omega value is in some embodiments calculated as described in the Example 1. Combinations of mutations are selected based on the results from screening of individual effect of single amino acid substitutions, as described above. Assuming that there is no interaction between active site residues, the effect of a given mutation is the same for both the parent polypeptide and any other mutant of the parent polypeptide. Therefore, for an enzyme, the product distribution profile upon another round of mutagenesis can easily be calculated using the following equation:

$$D_i = \frac{d_i x_i}{\sum_{j=1}^{n} d_j x_j} \times 100,$$

where $D_i$ is predicted percentage of product distribution of compound i, $d_i$ is experimentally measured or predicted percentage of product distribution of compound i, $x_i$ is the effect of a particular mutation on compound i productivity by the wild-type enzyme, and n represents the number of products considered (n=17). To maintain specific activity and productivity, the overall productivity was calculated using the following equation:

$$P = \sum_{i=1}^{n} P_i = \sum_{i=1}^{n} p_i x_i,$$

where P is total productivity, $P_i$ is predicted productivity for compound i, and $p_i$ is experimentally measured or predicted productivity for compound i. To select the mutation that likely introduces the desired function, the root mean square deviation of the predicted product distribution from desired product distribution is calculated using the following equation:

$$\omega = \sqrt{\frac{\sum_{i=1}^{n}(D_i - d_i')^2}{n}},$$

where ω represents the root mean square deviation or predicted product distribution by a particular mutation from the product distribution of the hypothetical enzyme with a desired function, and $d''_i$ is the percentage of desired product distribution for compound i. The mutations that reduce ω and maintain P are selectively and sequentially introduced into the parent polypeptide.

In some embodiments, the present invention provides a method of generating an enzyme variant that exhibits an altered product profile compared to a parent enzyme, the method generally involving: a) providing a library of amino acid sequences for candidate enzyme variants having one or more amino acid substitutions as compared to the parent enzyme, where each member of the library is assigned an omega value that has been determined from the empirically observed individual effect of the member's one or more substitutions on the function; and b) selecting at least one candidate from the library based on the at least one candidate's omega value, where the omega value of the at least one selected candidate is below the omega value for the parent enzyme, and where the variant enzyme comprises the candidate amino acid sequence and exhibits an altered product profile as compared to the parent enzyme.

In some embodiments, the parent enzyme is an enzyme that, upon-action on a single substrate, yields a plurality of (e.g., two or more, three or more, four or more, five or more, six or more, seven or more, eight or more, etc.) different products. In some embodiments, where the parent polypeptide is an enzyme that yields three or more different products upon catalytic action upon a single substrate, the variant enzyme is one that, upon catalytic action on the substrate, will preferentially yield two products from among the three or more products. For example, in some embodiments, the proportion of two products from among the three or more products is at least about 30%, at least about 40%, at least about 50%, at least about 60%, at least about 70%, at least about 80%, at least about 90%, at least about 95%, at least about 98%, at least about 99%, or more than about 99%, of the total yield of the three or more products. In some embodiments, where the parent polypeptide is an enzyme that yields a plurality of different products upon catalytic action upon a single substrate, the variant enzyme is one that, upon catalytic action on the substrate, will preferentially yield a single product from among the plurality of products. For example, in some embodiments, the proportion of the single product is at least about 30%, at least about 40%, at least about 50%, at least about 60%, at least about 70%, at least about 80%, at least about 90%, at least about 95%, at least about 98%, at least about 99%, or more than about 99%, of the total yield of the plurality of products.

In some embodiments, the present invention provides a method of generating an enzyme variant that exhibits an altered product profile compared to a parent enzyme, where the variant enzyme produces a product not produced by the parent enzyme. In some embodiments, where the parent polypeptide is an enzyme that yields at least a first product upon catalytic action on a substrate, the variant polypeptide yields a second product upon catalytic action on the substrate, where the second product is different from the first product. In other words, the variant polypeptide yields a product that the parent polypeptide does not yield. In many of these embodiments, the variant polypeptide preferentially yields the second product, e.g., the proportion of the second product yielded by the variant enzyme is at least about 30%, at least about 40%, at least about 50%, at least about 60%, at least about 70%, at least about 80%, at least about 90%, at least about 95%, at least about 98%, at least about 99%, or more than about 99%, of the total yield of products by the variant enzyme.

In some embodiments, the present invention provides a method of generating an enzyme variant that exhibits an altered substrate specificity compared to a parent enzyme, the method generally involving: a) providing a library of amino acid sequences for candidate enzyme variants having one or more amino acid substitutions as compared to the parent enzyme, where each member of the library is assigned an omega value that has been determined from the empirically observed individual effect of the member's one or more substitutions on the function; and b) selecting at least one candidate from the library based on the at least one candidate's omega value, where the omega value of the at least one selected candidate is below the omega value for the parent enzyme, and where the variant enzyme comprises the candidate amino acid sequence and exhibits an altered substrate specificity as compared to the parent enzyme.

In some embodiments, the present invention provides a method of generating a variant enzyme that exhibits altered substrate specificity, compared to a parent enzyme. In some embodiments, the parent polypeptide is an enzyme that yields a single product upon catalytic action on any of a plurality of substrates; and the variant enzyme exhibits altered substrate specificity. In some embodiments, where the parent polypeptide is an enzyme that yields a single product upon catalytic action upon any of a plurality of different substrates, the variant enzyme is one that will yield the single product by preferentially modifying a single substrate from among the plurality of substrates. For example, in some embodiments, the single product is produced by catalytic action of the variant enzyme preferentially on one substrate from among the plurality of substrates.

In some embodiments, the present invention provides a method of generating an enzyme variant that exhibits an altered substrate specificity and altered product profile compared to a parent enzyme, the method generally involving: a) providing a library of amino acid sequences for candidate enzyme variants having one or more amino acid substitutions as compared to the parent enzyme, where each member of the library is assigned an omega value that has been determined from the empirically observed individual effect of the member's one or more substitutions on the function; and b) selecting at least one candidate from the library based on the at least one candidate's omega value, where the omega value of the at least one selected candidate is below the omega value for the parent enzyme, and where the variant enzyme comprises the candidate amino acid sequence and exhibits an altered substrate specificity and altered product profile as compared to the parent enzyme.

In some embodiments, the present invention provides a method of generating a variant enzyme that exhibits altered substrate specificity and altered product profile, compared to a parent enzyme. In some embodiments, the parent polypeptide is an enzyme that produces a plurality of products from any of a plurality of substrates; and the variant enzyme is one that exhibits both altered substrate specificity and an altered product profile, compared to the parent enzyme. In some embodiments, where the parent polypeptide is an enzyme that yields a plurality of (e.g., two or more, three or more, four or more, five or more, six or more, seven or more, eight or more, etc.) different products upon catalytic action upon any of a plurality of different substrates. In some embodiments, where the parent polypeptide is an enzyme that yields three or more different products upon catalytic action upon any of a plurality of different substrates, the variant enzyme is one that, upon catalytic action preferentially on one substrate from among the plurality of substrates, will preferentially yield two products from among the three or more products. For example, in some embodiments, the proportion of two products from among the three or more products is at least about 30%, at least about 40%, at least about 50%, at least about 60%, at least about 70%, at least about 80%, at least about 90%, at least about 95%, at least about 98%, at least about 99%, or more than about 99%, of the total yield of the three or more products. In some embodiments, where the parent polypeptide is an enzyme that yields a plurality of different products upon catalytic action upon any of a plurality of different substrates, the variant enzyme is one that, upon catalytic action preferentially on one substrate from among the plurality of substrates, will preferentially yield a single product from among the plurality of products. For example, in some embodiments, the proportion of the single product is at least about 30%, at least about 40%, at least about 50%, at least about 60%, at least about 70%, at least about 80%, at least about 90%, at least about 95%, at least about 98%, at least about 99%, or more than about 99%, of the total yield of the plurality of products.

Computer Program Product and Computational Analysis System

The present invention provides a computer program product for carrying out a subject method for designing a variant polypeptide. The present invention also includes an algorithm for performing the subject methods, where the algorithm is recorded on a computer readable medium. The present invention further provides computational analysis systems that include a subject computer program product. The present invention further provides a kit for identifying a polypeptide variant.

One or more aspects of the above methodology may be in the form of computer readable media having programming stored thereon for implementing the subject methods. In other words, the subject methodology may be provided in the form of programming (a computer program product) or an algorithm recorded onto a computer readable medium. The computer readable media may be, for example, in the form of a computer disk or CD (compact disc), a floppy disc, a magnetic "hard card", a server, or any other computer readable media capable of containing data or the like, stored electronically, magnetically, optically or by other means. Accordingly, stored programming embodying steps for carrying-out the subject methods may be transferred to a computer such as a personal computer (PC), (i.e., accessible by a researcher or the like), by physical transfer of a CD, floppy disk, or like medium, or may be transferred using a computer network, server, or other interface connection, e.g., the Internet.

In some embodiments, a subject computer-readable medium has recorded thereon a program (a computer program product) that: a) assigns an omega value to each member of a library of amino acid sequences for candidate mutant polypeptides having one or more amino acid substitutions as compared to a parent polypeptide, wherein said omega value has been determined from the empirically observed individual effect of the member's two or more substitutions on a function of the polypeptide; and b) based on said at least one candidate's omega value, identifies at least one candidate from the library of amino acid sequences that exhibits altered function as compared to the parent polypeptide.

The present invention provides a computational analysis system comprising a subject computer-readable medium or a subject computer program product. In one embodiment of the subject invention, a system of the invention may include a single computer or the like with a stored algorithm capable of carrying out a subject method, i.e., a computational analysis system. In certain embodiments, the system is further characterized in that it provides a user interface, where the user interface presents to a user the option of selecting among one or more different, including multiple different, inputs, e.g., e.g., various parameter values for the algorithm, as described above, such as an omega value, etc. Computational systems that may be readily modified to become systems of the subject invention include those described in U.S. Pat. No. 6,251,588; the disclosure of which is herein incorporated by reference.

The present invention provides a kit for generating a polypeptide variant exhibiting altered function as compared to a parent polypeptide. A subject kit comprises a computer readable medium, as described above, which computer readable medium has an algorithm stored or recorded thereon, as described above; and instructions for using the algorithm to identify candidate mutant sequences, where a polypeptide comprising such a mutant sequence exhibits altered protein function as compared to a parent polypeptide.

Polypeptide Variants

The present invention provides variant terpene cyclases; and methods of producing the variant terpene cyclases. The present invention further provides compositions comprising a subject variant terpene cyclase.

A subject variant terpene cyclase catalyzes an enzymatic reaction, using a polyprenyl diphosphate as substrate. Polyprenyl diphosphate substrates that can serve as substrate for a subject variant terpene cyclase include, but are not limited to, geranyl diphosphate (GPP), farnesyl diphosphate (PP), geranylgeranyl diphosphate (GGPP), hexaprenyl diphosphate (HexPP), heptaprenyl diphosphate (HepPP), octaprenyl diphosphate (OPP), solanesyl diphosphate (SPP), decaprenyl diphosphate (DPP), nonaprenyl diphosphate (NPP), and undecaprenyl diphosphate (UPP) In some embodiments, the substrate of a subject variant terpene cyclase is GPP. In other embodiments, the substrate of a subject variant terpene cyclase is FPP. In other embodiments, the substrate of a subject variant terpene cyclase is GGPP.

In many embodiments, the product profile of a subject variant terpene cyclase is altered, compared to a parent terpene cyclase. For example, in some embodiments, a subject variant terpene cyclase modifies a polyprenyl diphosphate substrate to produce a product or a set of products that is different from the product or the set of products produced by the parent polypeptide, using the same polyprenyl diphosphate substrate.

In some embodiments, the substrate of a subject variant terpene cyclase is FPP. In some of these embodiments, a subject variant terpene cyclase produces a different product profile, compared to the parent polypeptide, e.g., a subject variant terpene cyclase preferentially produces a single product of enzymatic reaction on FPP, compared to the parent polypeptide.

As one non-limiting example, in some embodiments, the parent polypeptide is a γ-humulene synthase that catalyzes an enzymatic reaction with FPP as substrate, to produce at least 8 possible products, as shown in FIG. 1. In some embodiments, a subject variant terpene cyclase is a variant γ-humulene synthase, where the variant γ-humulene synthases preferentially produces one or two of the 8 products depicted in FIG. 1. In some embodiments, a subject variant terpene cyclase produces one of the 8 products depicted in FIG. 1 preferentially, e.g., at least about 20%, at least about 30%, at least about 40%, at least about 50%, at least about 60%, at least about 70%, at least about 80%, at least about 90%, at least about 95%, at least about 98%, or more, of the product produced by the variant terpene cyclase is one of the 8 products depicted in FIG. 1. In some embodiments, a subject variant terpene cyclase produces two of the 8 products depicted in FIG. 1 preferentially, e.g., at least about 20%, at least about 30%, at least about 40%, at least about 50%, at least about 60%, at least about 70%, at least about 80%, at least about 90%, at least about 95%, at least about 98%, or more, of the product produced by the variant terpene cyclase is two of the 8 products depicted in FIG. 1.

In some embodiments, the variant γ-humulene cyclase is a β-bisabolene synthase, e.g., the variant γ-humulene cyclase catalyzes a reaction, using FPP as a substrate, to preferentially produce β-bisabolene, compared to compounds 1-6 and 8 as depicted in FIG. 1. In some embodiments, the variant γ-humulene cyclase is a sibirene synthase, e.g., the variant γ-humulene cyclase catalyzes a reaction, using FPP as a substrate, to preferentially produce sibirene, compared to compounds 1 and 3-8 as depicted in FIG. 1. In some embodiments, the variant γ-humulene cyclase catalyzes a reaction, using FPP as a substrate, to preferentially produce γ-humulene, as compared to compounds 1, 2, and 4-8 as depicted in FIG. 1. In some embodiments, the variant γ-humulene cyclase is a longifolene synthase, e.g., the variant γ-humulene cyclase catalyzes a reaction, using FPP as a substrate, to preferentially produce longifolene, compared to compounds 1-3 and 5-8 as depicted in FIG. 1. In some embodiments, the variant γ-humulene cyclase is an α-longipinene synthase, e.g., the variant γ-humulene cyclase catalyzes a reaction, using FPP as a substrate, to preferentially produce α-longifolene, compared to compounds 1-4 and 6-8 as depicted in FIG. 1. In some embodiments, the variant γ-humulene cyclase is an E-β-farnesene/Z,E-α-farnesene synthase, e.g., the variant γ-humulene cyclase catalyzes a reaction, using FPP as a substrate, to preferentially produce compounds 1 and 8 as depicted in FIG. 1, compared to compounds 2-7 as depicted in FIG. 1.

In some embodiments, a subject variant terpene cyclase comprises an amino acid sequence as depicted in FIG. 12 and as set forth in SEQ ID NO:47. In some embodiments, a subject variant terpene cyclase comprises an amino acid sequence as depicted in FIG. 13 and as set forth in SEQ ID NO:48. In some embodiments, a subject variant terpene cyclase comprises an amino acid sequence as depicted in FIG. 14 and as set forth in SEQ ID NO:49. In some embodiments, a subject variant terpene cyclase comprises an amino acid sequence as depicted in FIG. 15 and as set forth in SEQ ID NO:50. In some embodiments, a subject variant terpene cyclase comprises an amino acid sequence as depicted in FIG. 16 and as set forth in SEQ ID NO:51. In some embodiments, a subject variant terpene cyclase comprises an amino acid sequence as depicted in FIG. 17 and as set forth in SEQ ID NO:52. In some embodiments, a subject variant terpene cyclase comprises an amino acid sequence as depicted in FIG. 18 and as set forth in SEQ ID NO:53. Those skilled in the art will recognize that subject variant terpene cyclases include polypeptides that differ in amino acid sequence from the sequences depicted in FIGS. 12-18. For example, in some embodiments, a subject variant terpene cyclase will comprise one or more amino acid substitutions compared to the amino acid sequence depicted in any one of FIGS. 12-18, e.g., a subject variant terpene cyclase will comprise one amino acid substitution, two amino acid substitutions, three amino acid substitutions, four amino acid substitutions, or from about five amino acid substitutions to about ten amino acid substitutions, compared to the amino acid sequence depicted in any one of FIGS. 12-18. In some embodiments, the one or more amino acid substitutions are conservative amino substitutions. In other embodiments, the one or more amino acid substitutions are not conservative amino acid substitutions. In some embodiments, the one or more amino acid substitutions do not substantially affect the product profile. In other embodiments, the one or more amino acid substitutions affect the product profile.

A subject variant terpene cyclase is a synthetic terpene cyclase, e.g., a subject variant terpene cyclase is a "recombinant" protein generated through human intervention. In many embodiments, the variant terpene cyclases are isolated; and in some embodiments, a subject variant terpene cyclase is pure, e.g., at least about 40% pure, at least about 50% pure, at least about 60% pure, at least about 70% pure, at least about 80% pure, at least about 90%, or at least about 95% or more pure.

A subject variant terpene cyclase is readily generated using well-established methods. A subject variant terpene cyclase can be produced synthetically, or can be produced recombinantly, i.e., a subject variant terpene cyclase-coding region can be inserted into an expression vector, and the coding region transcribed and translated, either in a living cell or in an in vitro transcription/translation system. One may employ solid phase peptide synthesis techniques, where such techniques are known to those of skill in the art. See Jones, The Chemical Synthesis of Peptides (Clarendon Press, Oxford) (1994). Generally, in such methods a peptide is produced through the sequential additional of activated monomeric units to a solid phase bound growing peptide chain.

A subject variant terpene cyclase can be produced recombinantly, e.g., a subject variant terpene cyclase-coding region can be inserted into an expression vector, and the coding region transcribed and translated, either in a living cell or in an in vitro transcription/translation system. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources. Expression vectors generally have convenient restriction sites located near the promoter sequence to provide for the insertion of nucleic acid sequences encoding heterologous proteins. A selectable marker operative in the expression host may be present.

A subject variant terpene cyclase may be produced in prokaryotes or eukaryotes in accordance with conventional ways, depending upon the purpose for expression. For large scale production of the variant terpene cyclase, a unicellular organism, such as E. coli, B. subtilis, S. cerevisiae, insect cells in combination with baculovirus vectors, or cells of a higher organism such as vertebrates, particularly mammals, e.g. COS 7 cells, may be used as the expression host cells. In some situations, it is desirable to produce the variant terpene cyclase in eukaryotic cells, where the protein will benefit from native folding and post-translational modifications. In other situations, it is desirable to produce the variant terpene cyclase in a prokaryotic cell, e.g., for production of an isoprenoid compound generated by action of the terpene cyclase on a polyprenyl diphosphate.

With the availability of a subject terpene cyclase in large amounts, e.g., by employing an expression host, the variant terpene cyclase may be isolated and purified in accordance with conventional ways. A lysate may be prepared of the expression host, and the lysate purified using high performance liquid chromatography, size exclusion chromatography, gel electrophoresis, affinity chromatography, or other purification technique.

The present invention further provides compositions comprising a subject variant terpene cyclase. Compositions comprising a subject variant terpene cyclase will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES),2-(N-Morpholino)ethanesulfonic acid sodium salt (MES),3-(N-Morpholino)propanesulfonic acid (MOPS), N-tris[Hydroxymethyl]methyl-3-aminopropanesulfonic acid (TAPS), etc., a solubilizing agent; a detergent, e.g., a non-ionic detergent such as Tween-20, etc.; a protease inhibitor; and the like.

Nucleic Acids, Vectors, and Host Cells

The present invention provides nucleic acids encoding a subject terpene cyclase variant, as well as recombinant vectors and recombinant host cells comprising the nucleic acids or recombinant vectors. In many embodiments, a subject nucleic acid is isolated, and is typically synthetic. In some embodiments, a subject nucleic acid is pure, e.g., at least about 50% pure, at least about 60% pure, at least about 70% pure, at least about 80% pure, at least about 90%, or at least about 95% or more pure. In many embodiments, a subject host cell is isolated. In some embodiments, a subject host cell is part of a multicellular organism. In other embodiments, a subject host cell is in vitro and is cultured as a unicellular entity.

A subject nucleic acid comprises a nucleotide sequence encoding a subject variant terpene cyclase. A subject recombinant vector comprises a subject nucleic acid. In many embodiments, a subject recombinant vector comprises a subject nucleic acid operably linked to one or more control elements, such as a promoter, a transcription terminator, and the like. A subject recombinant vector in some embodiments provides for amplification of the copy number of a subject nucleic acid. A subject recombinant vector is in some embodiments an expression vector that provides for synthesis of a subject variant terpene cyclase in a host cell, e.g., a prokaryotic host cell or a eukaryotic host cell.

In some embodiments, a subject nucleic acid comprises a nucleotide sequence that encodes a polypeptide comprising the amino acid sequence depicted in FIG. 12 and as set forth in SEQ ID NO:47. In some embodiments, a subject nucleic acid comprises a nucleotide sequence that encodes a polypeptide comprising the amino acid sequence depicted in FIG. 13 and as set forth in SEQ ID NO:48. In some embodiments, a subject nucleic acid comprises a nucleotide sequence that encodes a polypeptide comprising the amino acid sequence depicted in FIG. 14 and as set forth in SEQ ID NO:49. In some embodiments, a subject nucleic acid comprises a nucleotide sequence that encodes a polypeptide comprising the amino acid sequence depicted in FIG. 15 and as set forth in SEQ ID NO:50. In some embodiments, a subject nucleic acid comprises a nucleotide sequence that encodes a polypeptide comprising the amino acid sequence depicted in FIG. 16 and as set forth in SEQ ID NO:51. In some embodiments, a subject nucleic acid comprises a nucleotide sequence that encodes a polypeptide comprising the amino acid sequence depicted in FIG. 17 and as set forth in SEQ ID NO:52. In some embodiments, a subject nucleic acid comprises a nucleotide sequence that encodes a polypeptide comprising the amino acid sequence depicted in FIG. 18 and as set forth in SEQ ID NO:53.

In some embodiments, a subject nucleic acid comprises a nucleotide sequence that encodes a variant terpene cyclase, which variant terpene cyclase has at least about 75%, at least about 80%, at least about 90%, at least about 95%, at least about 98%, or at least about 99% amino acid sequence identity to the amino acid sequence depicted in any one of FIGS. 12-18, where nucleic acids comprising nucleotide sequences encoding the amino acid sequence depicted in FIG. 11 (and set forth in SEQ ID NO:46) are specifically excluded.

In many embodiments, a subject nucleic acid is an expression vector that includes a nucleic acid comprising a nucleotide sequence that encodes a subject variant terpene cyclase. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as E. coli and yeast). Thus, for example, a nucleic acid encoding a subject variant terpene cyclase is included in any one of a variety of expression vectors for expressing the variant terpene cyclase. Such vectors include chromosomal, nonchromosomal and synthetic DNA sequences.

Numerous suitable expression vectors are known to those of skill in the art, and many are commercially available. The following vectors are provided by way of example; for bacterial host cells: pQE vectors (Qiagen),% pBluescript plasmids, pNH vectors, lambda-ZAP vectors (Stratagene); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

The variant terpene cyclase-encoding nucleotide sequence in the expression vector is operably linked to an appropriate expression control sequence(s) (promoter) to direct synthesis of the encoded variant terpene cyclase. Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

Suitable promoters for use in prokaryotic host cells include, but are not limited to, a bacteriophage T7 RNA polymerase promoter; a trp promoter; a lac operon promoter;

a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367-378); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In addition, the expression vectors will in many embodiments contain one or more selectable marker genes to provide a phenotypic trait for selection of transformed host cells such as dihydrofolate reductase or neomycin resistance for eukaryotic cell culture, or such as tetracycline or ampicillin resistance in prokaryotic host cells such as *E. coli*.

Generally, recombinant expression vectors will include origins of replication and selectable markers permitting transformation of the host cell, e.g., the ampicillin resistance gene of *E. coli*, the *S. cerevisiae* TRP1 gene, etc.; and a promoter derived from a highly-expressed gene to direct transcription of the variant terpene cyclase-encoding sequence. Such promoters can be derived from operons encoding glycolytic enzymes such as 3-phosphoglycerate kinase (PGK), α-factor, acid phosphatase, or heat shock proteins, among others.

In many embodiments, a subject nucleic acid includes a nucleotide sequence encoding a subject variant terpene cyclase, where the nucleotide sequence encoding the variant terpene cyclase is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In many embodiments, a subject nucleic acid includes a nucleotide sequence encoding a subject variant terpene cyclase, where the nucleotide sequence encoding the variant terpene cyclase is operably linked to a constitutive promoter. Suitable constitutive promoters for use in prokaryotic cells are known in the art and include, but are not limited to, a sigma70 promoter, e.g., a consensus sigma70 promoter.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast Saccharomyces, 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

The present invention provides genetically modified host cells, where a subject genetically modified host cell comprises a subject nucleic acid or a subject recombinant vector. Genetically modified host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like.

In other embodiments, the genetically modified host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270:299-302. Examples of Salmonella strains which can be employed in the present invention include, but are not limited to, *Salmonella typhi* and *S. typhimurium*. Suitable Shigella strains include, but are not limited to, *Shigella flexneri, Shigella sonnei,* and *Shigella disenteriae*. Typically, the laboratory strain is one that is non-pathogenic. Non-limiting examples of other suitable bacteria include, but are not limited to, *Pseudomonas pudita, Pseudomonas aeruginosa, Pseudomonas mevalonii, Rhodobacter sphaeroides, Rhodobacter capsulatus, Rhodospirillum rubrum, Rhodococcus* sp., and the like.

To generate a genetically modified host cell, a subject nucleic acid or a subject recombinant vector is introduced stably or transiently into a host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

A subject genetically modified host cell is useful for producing a terpenoid compound, as described below. For the production of a terpenoid compound, a host cell is one that produces, or has been genetically modified to produce, a polyprenyl diphosphate that is a substrate of a subject variant terpene cyclase. In some embodiments, the host cell is one that produces a polyprenyl diphosphate substrate of a subject variant terpene cyclase via a mevalonate pathway. In other embodiments, the host cell is one that produces a polyprenyl diphosphate substrate of a subject variant terpene cyclase via a DXP pathway.

In some embodiments, a genetically modified host cell is a host cell that comprises an endogenous mevalonate pathway. In other embodiments, a genetically modified host cell is a host cell that does not normally produce mevalonate or IPP via a mevalonate pathway, but has been genetically modified with one or more nucleic acids comprising nucleotide sequences encoding one or more mevalonate pathway enzymes. See, e.g., U.S. Patent Publication No. 2004/005678; U.S. Patent Publication No. 2003/0148479; Martin et al. (2003) *Nat. Biotech.* 21(7):796-802.

In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding acetoacetyl-CoA thiolase; hydroxymethylglutaryl-CoA (HMG-CoA) synthase; and HMG-CoA reductase. In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding acetoacetyl-CoA thiolase; HMG-CoA synthase; HMG-CoA reductase; mevalonate kinase; phosphomevalonate kinase; and mevalonate pyrophosphate decarboxylase. In some embodiments, a suitable host cell is a host cell that does not normally produce mevalonate or IPP via a mevalonate pathway, but has been genetically modified to produce mevalonate, or IPP, via a mevalonate pathway, e.g., has been genetically modified with one or more nucleic acids comprising nucleotide sequences encoding mevalonate kinase; phosphomevalonate kinase; and mevalonate pyrophosphate decarboxylase. In some of these embodiments, the host cell has been further genetically modified with a nucleic acid comprising a nucleotide sequence encoding a polyprenyl diphosphate synthase, e.g., FPP synthase, GPP synthase, GGPP synthase, and the like. In some embodiments, the DXP pathway of the host cell has been functionally disabled.

The present invention further provides compositions comprising a subject nucleic acid. Compositions comprising a subject nucleic acid will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES),2-(N-Morpholino) ethanesulfonic acid (MES),2-(N-Morpholino)ethanesulfonic acid sodium salt (MES),3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like.

The present invention further provides compositions comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

Methods of Producing Isoprenoid Compounds

The present invention provides methods of producing isoprenoid compounds in a host cell. The methods generally involve culturing a subject genetically modified host cell in a suitable culture medium under conditions that promote synthesis of an isoprenoid compound, where the isoprenoid compound is generated by action of a subject variant terpene cyclase, which cyclase is produced in the genetically modified host cell, on a polyprenyl diphosphate substrate present in the host cell. In some embodiments, a subject method further comprises isolating the isoprenoid compound from the cell and/or from the culture medium.

In some embodiments, a subject genetically modified host cell is cultured in a suitable medium (e.g., Luria-Bertoni broth, optionally supplemented with one or more additional agents, such as an inducer (e.g., where the variant terpene cyclase is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the variant terpene cyclase-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound will be separated from other products which may be present in the organic layer. Separation of the isoprenoid compound from other products that may be present in the organic layer is readily achieved using, e.g., standard chromatographic techniques.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid compounds, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Designing and generating terpene cyclase variants

Methods

Reagents and equipments. All enzymes and chemicals were purchased from New England Biolabs and Sigma-Aldrich Co, respectively, unless otherwise stated. An HP6890 gas chromatograph equipped with a 5973 mass selective detector (Hewlett Packard), a CyclosilB capillary column (30 m×250 μm i.d.×0.25 μm thickness, Agilent Technologies), and a Combi PAL auto sample-injector (LEAP Technologies) were used for sesquiterpene analysis. An LS6500 multi-purpose scintillation counter (Beckman coulter) was used for enzyme kinetics.

Synthesis of γ-humulene cyclase gene. The γ-humulene cyclase gene used herein was designed to maintain the native (wild-type) primary amino acid sequence but with optimized codon usage for E. coli; the gene was synthesized from oligonucleotides using standard methods. The synthetic gene was digested with NcoI/XbaI, and cloned into pTrc99A to form pTrcHUM. The vector was transformed into E. coli DH10B, and the transformants were screened for sesquiterpene production. Several functional clones were found and sequenced. For high-level production of the target enzyme, the gene encoding γ-humulene cyclase was cut from pTrcHUM with NcoI/HindIII, and cloned into pET29 (Strategene) to form pETHUM. The nucleotide sequence of the codon-optimized γ-humulene coding sequence is depicted in FIG. 10.

GC-MS analysis for sesquiterpenes. A single colony was inoculated into Luria Bertani (LB) medium containing 50 μg/ml carbenicillin (Cb) and grown overnight at 30° C. An aliquot (50μl) of this seed culture was inoculated into fresh LB medium containing Cb (5 ml), overlaid with 500 μl dodecane, and grown for 24 hours at 30° C. An aliquot of dodecane (50 μl) was diluted into 200 μl of ethyl acetate, and the mixture was analyzed by GC-MS using a GC oven temperature program of 80° C. for 1 min, then ramping 30° C./min to 110° C., 5° C./min to 160° C., and 130° C./min to 250° C. Sesquiterpenes were identified from their mass spectra and GC retention times by comparison to available authentic standards and spectra in libraries previously reported in the literature.

Homology structural modeling of γ-humulene cyclase. The homology structural model for γ-humulene cyclase was built using MODELLER. Baker and Sali (2001)*Science* 294:93-96. The alignment and the structure of 5-epi-aristolochene cyclase (Starks et al. (1997) *Science* 277:1815-1820) (PDBentry 5 eat) were used as guides.

Saturation and site directed mutagenesis of γ-humulene cyclase by overlap polymerase chain reaction (PCR). Both saturation and site directed mutagenesis were carried out using overlap PCR. Ho et al. (1989) *Gene* 77:51-59. Forward (F) and reverse (R) primer sequences are shown in Table 1.

TABLE 1

| Primer Name | Sequences(5'→3') | SEQ ID NO: |
|---|---|---|
| HUM-W312SatF | CGTAAATGCTATGTGGAANNNTACTTCTGGATGGCCGCG | 1 |
| HUM-W312SatR | CGCGGCCATCCAGAAGTANNNTTCCACATAGCATTTACG | 2 |
| HUM-W315SatF | TATGTGGAATTTTACTTCNNNATGGCCGCGGCAATTTCA | 3 |
| HUM-W315SatR | TGAAATTGCCGCGGCCATNNNGAAGTAAAATTCCACATA | 4 |
| HUM-A336SatF | GTGGCATTCACTAAAATTNNNATCTTGATGACAATGTTA | 5 |
| HUM-A336SatR | TAACATTGTCATCAAGATNNNAATTTTAGTGAATGCCAC | 6 |
| HUM-M339SatF | ACTAAAATTGCGATCTTGNNNACAATGTTAGATGACTTA | 7 |
| HUM-M339SatR | TAAGTCATCTAACATTGTNNNCAAGATCGCAATTTTAGT | 8 |
| HUM-T340SatF | AAAATTGCGATCTTGATGNNNATGTTAGATGACTTATAC | 9 |
| HUM-T340SatR | GTATAAGTCATCTAACATNNNCATCAAGATCGCAATTTT | 10 |
| HUM-Y419SatF | GAACGCTATCTGGAAGCGNNNTTGCAGGATGCCGAATGG | 11 |
| HUM-Y419SatR | CCATTCGGCATCCTGCAANNNCGCTTCCAGATAGCGTTC | 12 |
| HUM-T445SatF | AACAATGGCACCCCCAACNNNGGTATGTGTGTACTTAAT | 13 |

TABLE 1-continued

| Primer Name | Sequences(5'→3') | SEQ ID NO: |
|---|---|---|
| HUM-T445SatR | ATTAAGTACACACATACCNNNGTTGGGGGTGCCATTGTT | 14 |
| HUM-G446SatF | AATGGCACCCCCAACACCNNNATGTGTGTACTTAATCTG | 15 |
| HUM-G446SatR | CAGATTAAGTACACACATNNNGGTGTTGGGGGTGCCATT | 16 |
| HUM-M447SatF | GGCACCCCCAACACCGGTNNNTGTGTACTTAATCTGATC | 17 |
| HUM-M447SatR | GATCAGATTAAGTACACANNNACCGGTGTTGGGGGTGCC | 18 |
| HUM-L450SatF | AACACCGGTATGTGTGTANNNAATCTGATCCCGTTGCTG | 19 |
| HUM-L450SatR | CAGCAACGGGATCAGATTNNNTACACACATACCGGTGTT | 20 |
| HUM-S484SatF | CATCTGATTGAACTGGCTNNNCGACTGGTCGATGATGCG | 21 |
| HUM-S484SatR | CGCATCATCGACCAGTCGNNNAGCCAGTTCAATCAGATG | 22 |
| HUM-V487SatF | GAACTGGCTAGCCGACTGNNNGATGATGCGAGAGATTTT | 23 |
| HUM-V487SatR | AAAATCTCTCGCATCATCNNNCAGTCGGCTAGCCAGTTC | 24 |
| HUM-L558SatF | AAATACTCATTCCACGTCNNNGCGCGGTCGATTCAGTTT | 25 |
| HUM-L558SatR | AAACTGAATCGACCGCGCNNNGACGTGGAATGAGTATTT | 26 |
| HUM-I562SatF | CACGTCCTGGCGCGGTCGNNNCAGTTTATGTATAACCAG | 27 |
| HUM-I562SatR | CTGGTTATACATAAACTGNNNCGACCGCGCCAGGACGTG | 28 |
| HUM-M565SatF | GCGCGGTCGATTCAGTTTNNNTATAACCAGGGGGACGGG | 29 |
| HUM-M565SatR | CCCGTCCCCCTGGTTATANNNAAACTGAATCGACCGCGC | 30 |
| HUM-Y566SatF | CGGTCGATTCAGTTTATGNNNAACCAGGGGGACGGGTTT | 31 |
| HUM-Y566SatR | AAACCCGTCCCCCTGGTTNNNCATAAACTGAATCGACCG | 32 |
| HUM-D570SatF | TTTATGTATAACCAGGGGNNNGGGTTTTCGATTTCGAAC | 33 |
| HUM-D570SatR | GTTCGAAATCGAAAACCCNNNCCCCTGGTTATACATAAA | 34 |
| HUM-F572SatF | TATAACCAGGGGACGGGNNNTCGATTTCGAACAAAGTT | 35 |
| HUM-F572SatR | AACTTTGTTCGAAATCGANNNCCCGTCCCCCTGGTTATA | 36 |
| HUM-Y573SatF | AACCAGGGGACGGGTTTNNNATTTCGAACAAAGTTATT | 37 |
| HUM-Y573SatR | AATAACTTTGTTCGAAATNNNAAACCCGTCCCCCTGGTT | 38 |
| HUM-M565I/V/L-F | GCGCGGTCGATTCAGTTTVTTTATAACCAGGGGGACGGG | 39 |
| HUM-M565I/V/L-R | CCCGTCCCCCTGGTTATAAABAAACTGAATCGACCGCGC | 40 |
| HUM-A336CF | GTGGCATTCACTAAAATTTGCATCTTGATGACAATGTTA | 41 |
| HUM-A336CR | TAACATTGTCATCAAGATGCAAATTTTAGTGAATGCCAC | 42 |
| HUM-T445CF | CTGAACAATGGCACCCCCAACTGCGGTATGTGTGTACTTAATCTG | 43 |
| HUM-T445CR | CAGATTAAGTACACACATACCGCAGTTGGGGGTGCCATTGTTCAG | 44 |

N- and C-terminal fragments were amplified by PCR: 94° C. for 30 sec, 50° C. for 30 sec, and 68° C. for 2 min, repeated 30 times. The reaction mixture contained Pfu buffer, 2 mM dNTP, 0.5 μM forward and reverse primers, 2.5 U Pfu turbo (Strategene), and 50 ng pTrcHUM in 100 μl. Amplified DNA was gel purified using a kit (Qiagen). Overlap PCR30 was carried out using the protocols described above. The fully amplified fragment was digested with NcoI/XbaI and cloned into pTrc99A.

The algorithm for systematic remodeling of plasticity residues. To design the specificity for novel sesquiterpene cyclases, combinations of mutations were selected based on the results from the previous screening. Assuming that there is no interaction between active site residues, the effect of a certain mutation is the same for both wild-type and other mutants. Therefore, the product distribution profile upon another round of mutagenesis can easily be calculated using the following equation:

$$D_i = \frac{d_i x_i}{\sum_{j=1}^{n} d_j x_j} \times 100,$$

where $D_i$ is predicted percentage of product distribution of compound i, $d_i$ is experimentally measured or predicted percentage of product distribution of compound i, $x_i$ is the effect of a particular mutation on compound i productivity by the wild type enzyme (FIG. 3a-c), and n represents the number of products considered (n=17). To maintain specific activity and productivity, the overall productivity was calculated using the following equation:

$$P = \sum_{i=1}^{n} P_i = \sum_{i=1}^{n} p_i x_i,$$

where P is total productivity, $P_i$ is predicted productivity for compound i, and $p_i$ is experimentally measured or predicted productivity for compound i. To select the mutation that likely introduces the desired function, the root mean square deviation of the predicted product distribution from desired product distribution was calculated using the following equation:

$$\omega = \sqrt{\frac{\sum_{i=1}^{n}(D_i - d_i')^2}{n}},$$

where ω represents the root mean square deviation or predicted product distribution by a particular mutation from the product distribution of the hypothetical enzyme with a desired function, and d', is the percentage of desired product distribution for compound i (e.g. for β-bisabolene cyclase, $d'_7=100\%$ and $d'_{i \neq 7}=0\%$). The mutations that reduce ω and maintain P are selectively and sequentially introduced into the wild type γ-humulene cyclase.

Protein expression and purification. Wild type γ-humulene cyclase and its variants were cloned into pET29 and transformed into BL21(DE3). Each transformant was inoculated into LB medium (5 ml) containing 50 µg/ml kanamycin (Km) and was grown overnight at 30° C. An aliquot (2 ml) of this seed culture was inoculated into fresh terrific both (TB) medium containing Km (500 ml), and the culture was grown at 30° C. When the culture reached $OD_{600nm}$ of 0.6-0.8, 0.05 mM of IPTG was added, and it was grown at 20° C. for 16 hours. Cells were harvested by centrifugation at 6,000×g for 15 min. The pellet was suspended in 10-15 ml of BugBuster (Novagen) containing 20 U DNaseI and bacterial protease inhibitor, and was incubated for two hours at 4° C. The solution was then centrifuged at 20,000×g for 30 min, and was filtered through a 0.45-µm filter. S-tag™ Thrombin purification kit (Novagen) was used for the purification following the protocol recommended by Novagen. All purifications were done at half scale. The eluted protein solution was dialyzed twice (PIERCE, MW 3,000 Da) against 1 L of buffer containing 10 mM Tes (pH 7.0), 10 mM $MgCl_2$, 1 mM DTT and 5% glycerol overnight. The protein concentration was measured by Bradford assay. Approximately 3 ml of 25-500 µg/ml of protein solution with about 95% purity was obtained (confirmed by sodium dodecyl sulfate-polyacrylamide gel electrophoresis (SDS-PAGE) gel analysis).

Enzyme Kinetics. Kinetics for each enzyme was measured in a 40 µl reaction containing 58.6 µM farnesyl pyrophosphate (FPP) (15 µCi/ml, [$^3$H]FPP), 0.05-0.50µM enzyme, in buffer described in previous section and overlaid with dodecane. The reaction mixture was incubated for 20 minutes at 31° C. To stop the reaction, 40 µL of a solution containing 4 M NaOH and 1 M EDTA was added and mixed. To extract sesquiterpene products, the reaction mixture was vortexed for 1 min, and 400 µL of dodecane was taken from the solution and mixed with 10 mL of scintillation fluid. Radioactivity was measured by scintillation counting. $k_{cat}$, $K_m$ and $k_{cat}/K_m$ were calculated using Enzyme Kinetics!Pro (ChemSW).

Results

To investigate how promiscuous proteins evolved to acquire more active and specific functions, the sesquiterpene γ-humulene cyclase from Abies grandis was chosen as a model protein. Steele et al. (1998) J. Biol. Chem. 273:2078-2089; and Little and Croteau (2002) Arch. Biochem. Biophys. 402:120-135. The sesquiterpene γ-humulene cyclase from Abies grandis has been shown to produce 52 different sesquiterpenes from a sole substrate, farnesyl pyrophosphate (FPP), through several cyclization mechanisms (FIG. 1). All terpene cyclases share a similar active site scaffold, called the terpene fold. Lesburg et al. (1997) Science 277:1820-1824; Starks et al. (1997) Science 277:1815-1820; Caruthers et al. (2000) J. Biol. Chem. 275:25533-25539; Rynkiewicz et al. (2001) Proc. Natl. Acad. Sci. USA 98:13543-13548. Prenyl diphosphate substrate binds to the active site through magnesium ions chelated by conserved aspartate-rich-motif. The reaction is initiated by the cleavage of the pyrophosphate group, which results in the formation of a carbocation intermediate. This intermediate is then cyclized into many different structures; however, the mechanisms by which terpene cyclases stabilize and direct such highly reactive and complex carbocation species to their multiple products is still not understood. The reaction is quenched by proton abstraction from nearby residues. Since over 200 sesquiterpene structures with different regio- and stereochemistries are synthesized from those enzymatic reactions (Glasby Encyclopaedia of the Terpenoids Wiley, Chichester, N.Y., 1982), sesquiterpene cyclases are an excellent model to study plasticity residues.

FIG. 1. γ-Humulene cyclase cyclization reaction mechanisms. When the substrate, farnesyl diphosphate, binds to the enzyme active site via magnesium, the diphosphate group is released to yield the cisoid-farnesyl cation. From this cation, sibirene (2) is produced by the 10,1 cyclization reaction. This cation is then isomerized to a transoid configuration. From this cation, γ-humulene (3), longifolene (4), and α-longipinene (5) are produced through an 11,1 cyclization reaction, α-ylangene (6) through a 10,1 cyclization reaction, β-bisabolene (7) through a 6,1 initial cyclization reaction. E-β-farnesene (1) and Z,E-α-farnesene (8) can be produced by directed deprotonation from either cation.

To determine the active-site residues important for γ-humulene cyclase activity, a homology structure for γ-humulene cyclase was first built using the crystal structure of 5-epi-aristolochene cyclase (PDBentry 5 eat; Starks et al. (1997) Science 277:1815-1820) as a guide. Baker and Sali (2001) supra; and Rynkiewicz et al. (2002) supra. Although mutations to residues in the conserved aspartate-rich-motif in the active site are known to alter the reaction mechanisms of terpene cyclases (Little and Croteau (2002) supra; and Joo et al. (1999) Nature 399:670-673), these residues were not considered further, because mutations in this motif are usually accompanied by significant losses of activity (Little and Croteau (2002) supra; and Joo et al. (1999) supra). Indeed, any residues thought to decrease the activity were not considered. As a result, the 19 residues composing the active site contour were selected for saturation mutagenesis studies (FIG. 2) to investigate how each residue contributes to a particular reaction mechanism.

Figure 2:
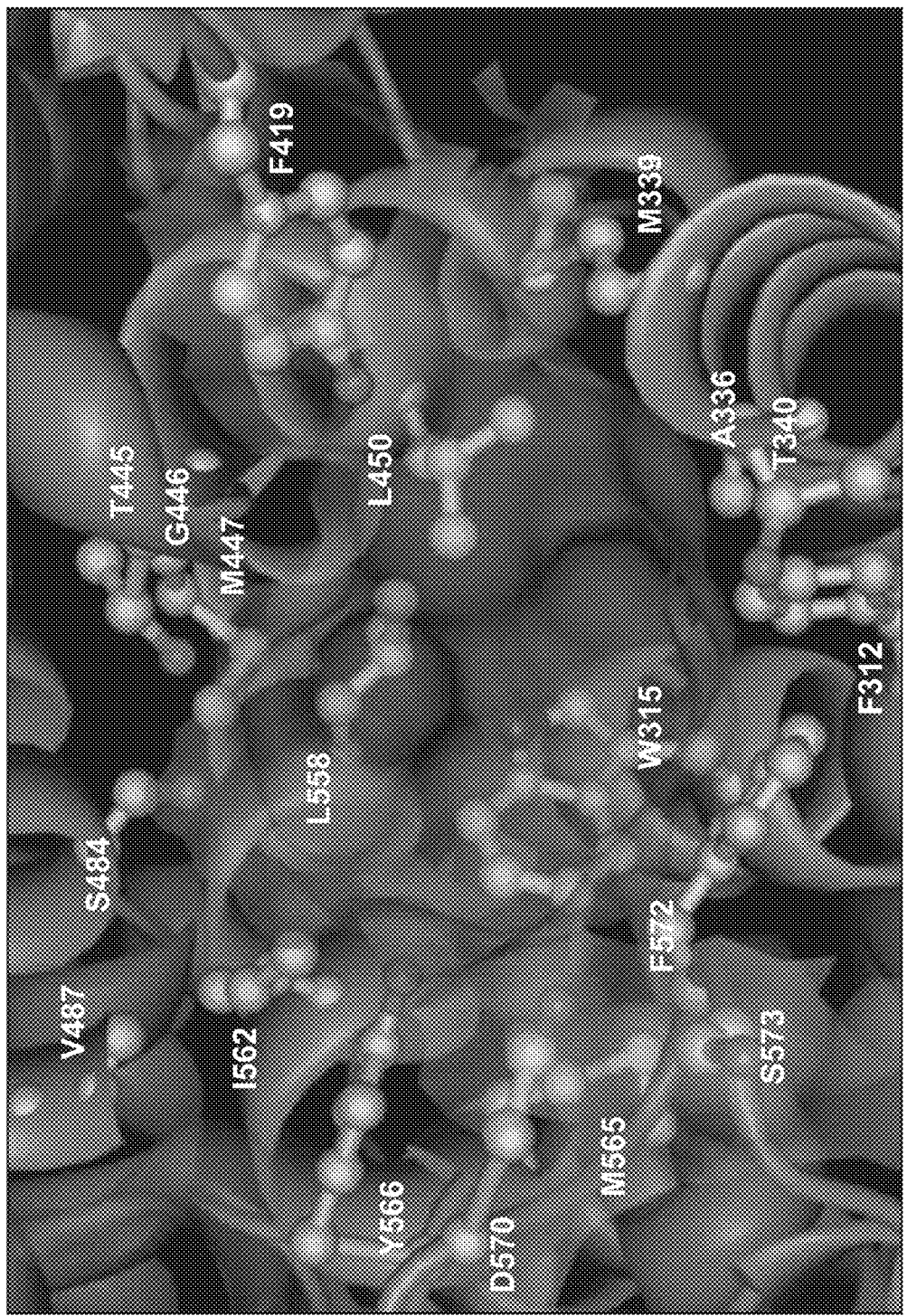
FIG. 2 depicts the homology structural model for the γ-humulene cyclase active site.

FIG. 2. The homology structural model for γ-humulene cyclase active site. The model was built using MODELLER (on the internet at salilab.org/modeler) with 5-epi-aristolochene cyclase as a guide. The homology structure was visualized using Chimera (on the world wide web at cgl.ucsf.edu/chimera). The 19 residues in the active site and the surface made by those residues are shown with transparency. These residues were the target for saturation mutagenesis and systematic plasticity residue remodeling. Residues in the aspartate rich motif, which are generally conserved in all sesquiterpene cyclases, were excluded, because mutations to these residues have been shown to significantly decrease enzyme activity.

Approximately 80 mutants for each of 19 residues mutated were screened by GC-MS. The results are depicted in FIGS. 3-6.

Figure 3:
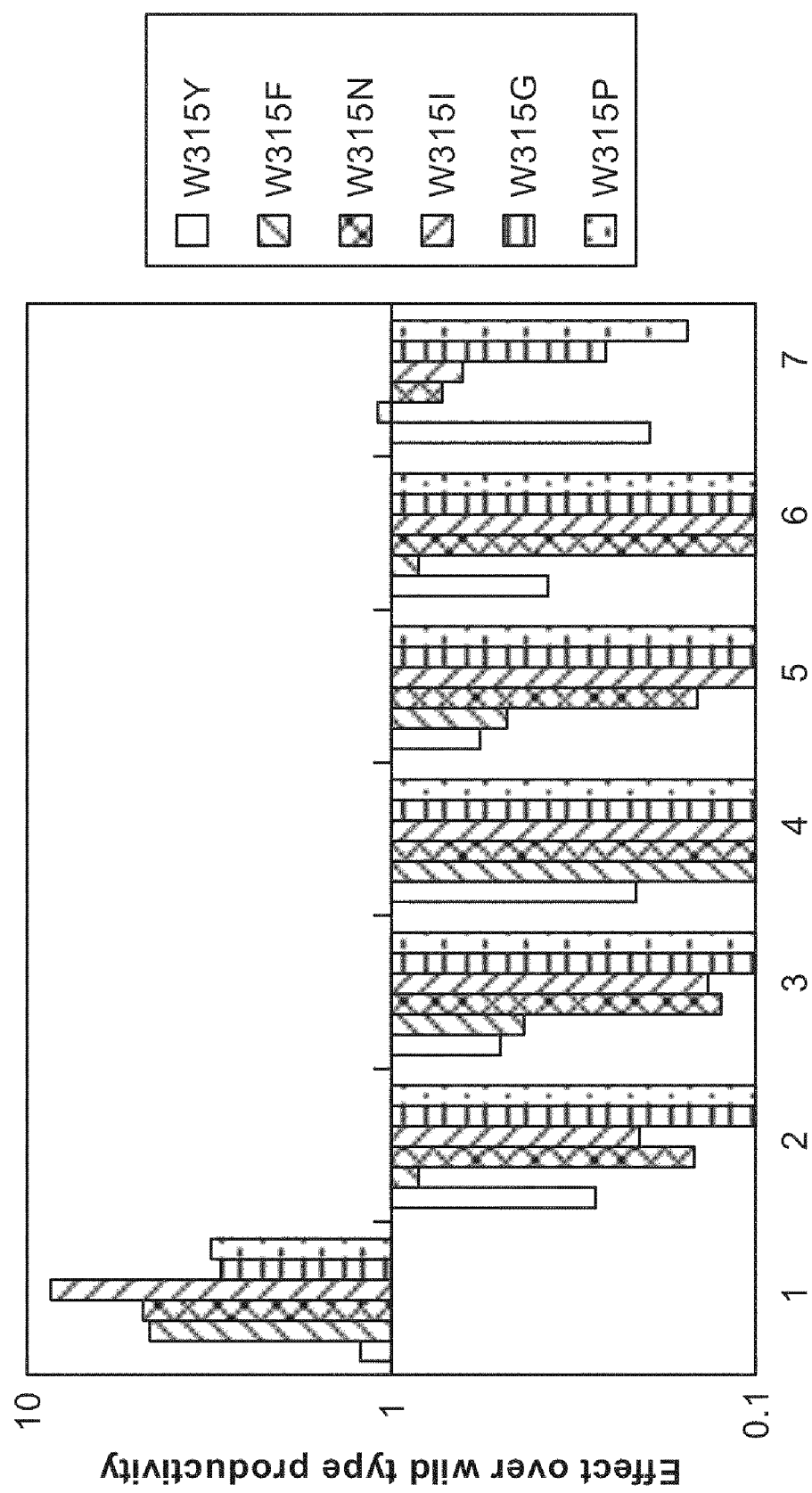
FIG. 3 depicts the effect of single amino acid substitutions at amino acid 315 of γ-humulene cyclase on production of compounds 1-7 shown in FIG. 1, compared to production of compounds 1-7 by wild-type γ-humulene cyclase.

As shown in FIG. 3, W315 was found to be very important for cyclic sesquiterpene formation. As both size and polarity of the residues in this position decreased, the enzyme produced more acyclic sesquiterpenes. The effect was very similar to what was observed for mutagenesis of Y92 of aristolochene cyclase. Calvert et al. (2002) *Chem. Commun. (Camb.)* 20:2384-2385; and Deligeorgopoulou et al. (2003) *Biochem.* 42:7741-7747. W315 prevents FPP from binding in an elongated form and provides electrostatic stabilization for different cyclic cations formed from the initial cyclization reactions. Interestingly, W315 is conserved in all sesquiterpene cyclases that catalyze the formation of cyclic sesquiterpenes. W315 is, however, less conserved in farnesene synthases. With W315P, the E-β-farnesene (1)/Z,E-α-farnesene (8) synthase with higher specific activity was constructed.

Figure 4:
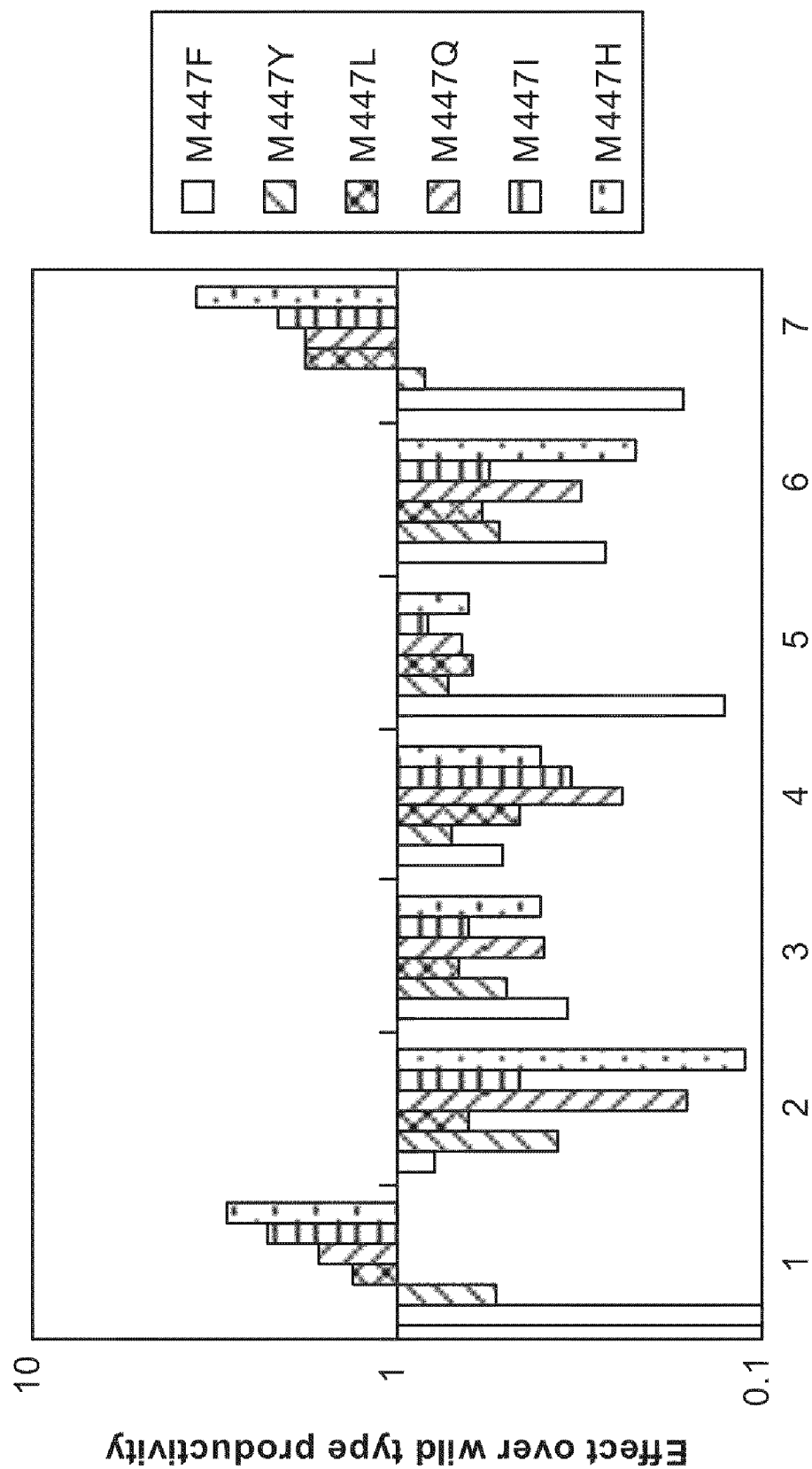
FIG. 4 depicts the effect of single amino acid substitutions at amino acid 447 of γ-humulene cyclase on production of compounds 1-7 shown in FIG. 1, compared to production of compounds 1-7 by wild-type γ-humulene cyclase.

As shown in FIG. 4, M447 was shown to determine the reaction specificity to either the 10, 1 or 6,1 cyclization reaction from the cisoid or transoid farnesyl cation, respectively. The reaction pathways can be distinguished by monitoring the downstream products sibirene (2) and β-bisabolene (7), respectively (FIG. 3). Generally, bulk hydrophobic residues, such as Phe, had higher selectivity to 2, whereas hydrophilic residues, such as H is, showed higher selectivity to 7.

Figure 5:
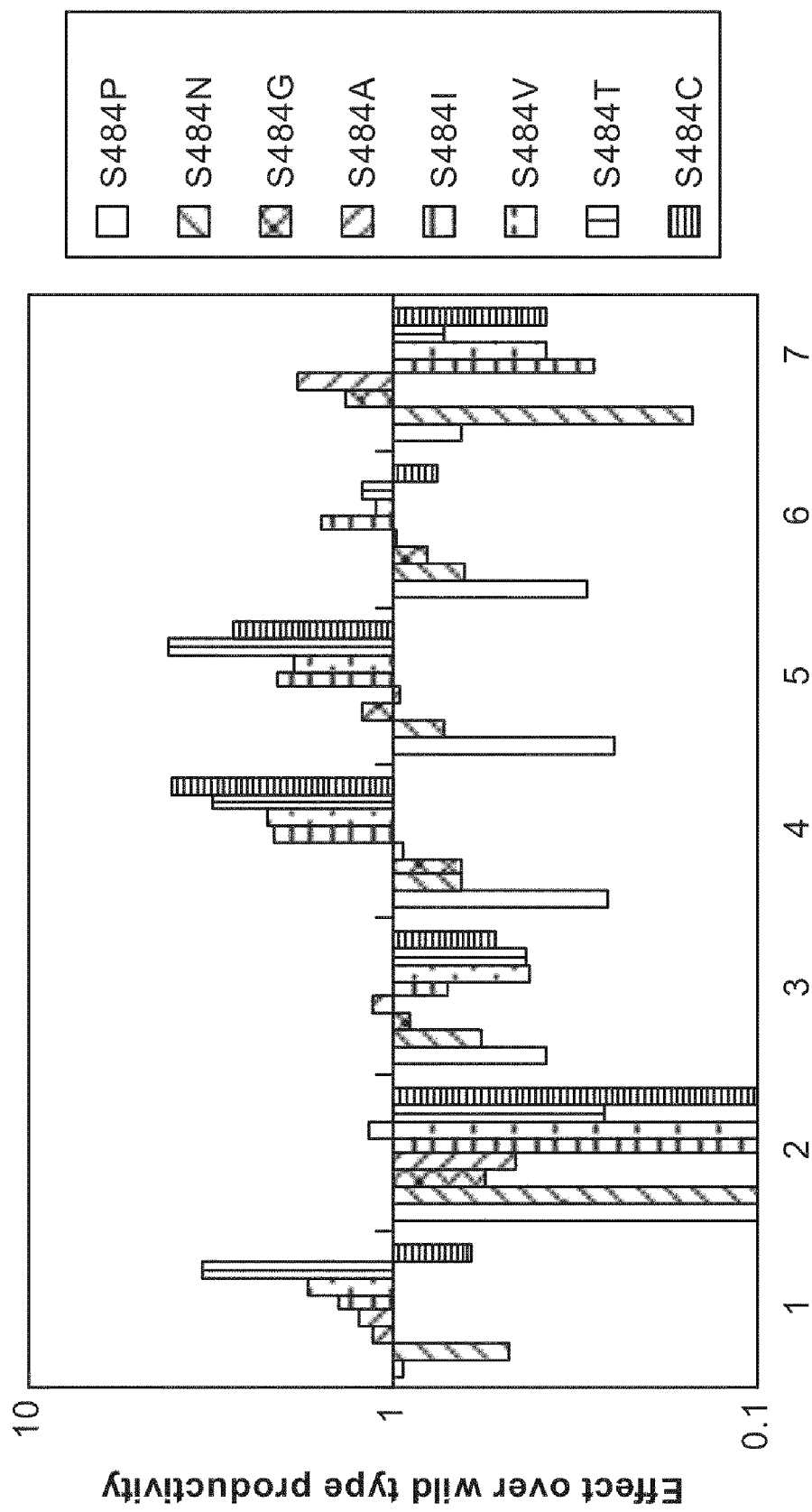
FIG. 5 depicts the effect of single amino acid substitutions at amino acid 484 of γ-humulene cyclase on production of compounds 1-7 shown in FIG. 1, compared to production of compounds 1-7 by wild-type γ-humulene cyclase.

As shown in FIG. 5, S484 was shown to be important in selectivity between the 10,1 and 11,1 cyclization reactions from the cisoid or transoid farnesyl cation, respectively. The 11,1 cyclization reaction was monitored by production of γ-humulene (3), longifolene (4), and α-longipinene (5). The more hydrophobic and polar the residue in this position, such as Thr and Cys, the more products from the 11,1 cyclization reaction became dominant. It is also interesting to note that S484C produced 4 as its major product; hence it is also important in secondary and tertiary cyclization reactions. Since the corresponding residue to S484 in longifolene cyclase from Norway spruce (Martin et al. (2004) *Plant Physiol.* 135:1908-1927) is not Cys, mutation to Cys may improve selectivity to 4 significantly.

Figure 6:
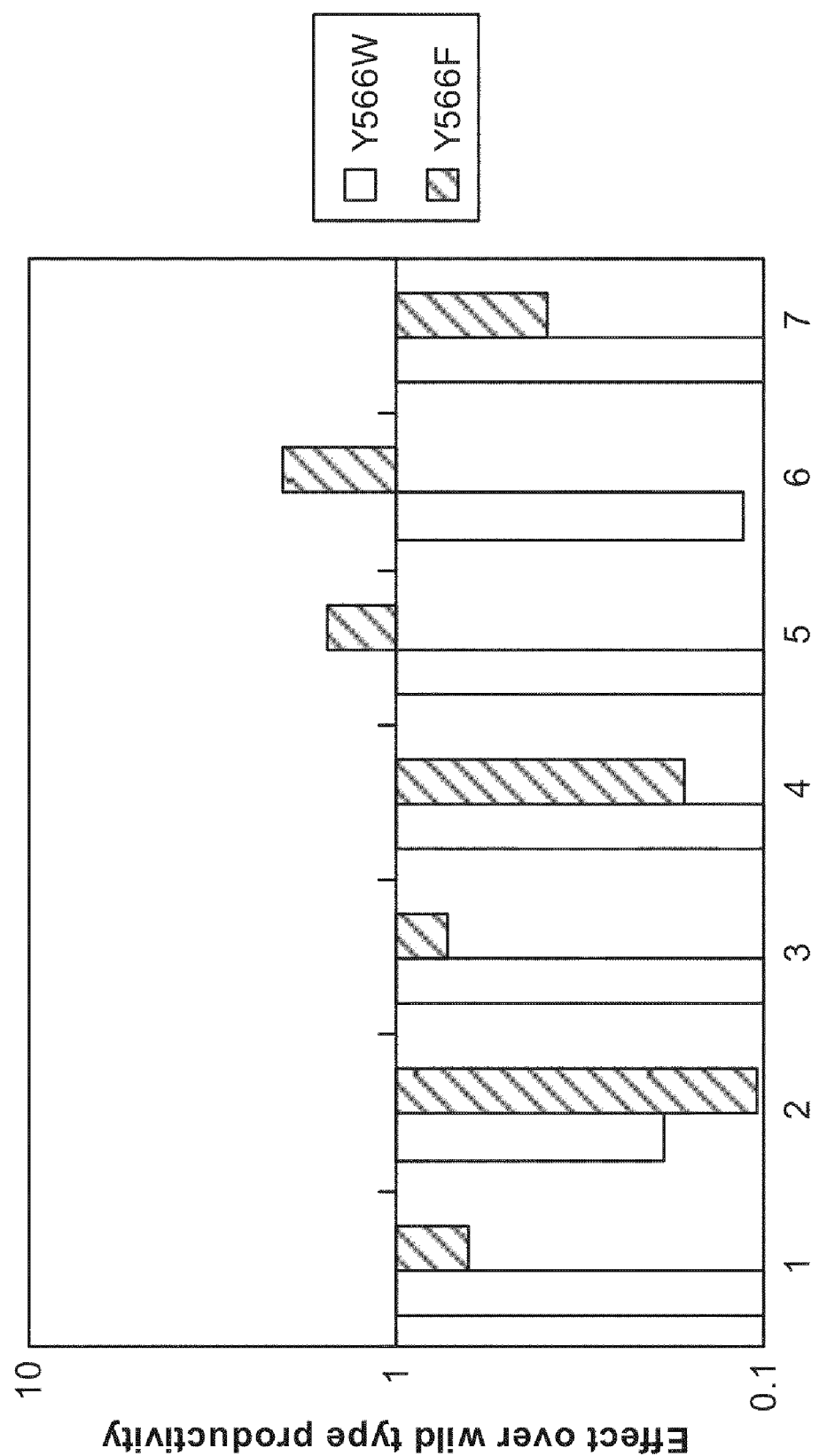
FIG. 6 depicts the effect of single amino acid substitutions at amino acid 566 of γ-humulene cyclase on production of compounds 1-7 shown in FIG. 1, compared to production of compounds 1-7 by wild-type γ-humulene cyclase.

As shown in FIG. 6, Y566 was shown to be important in selectivity between the 10,1 cyclization reactions from the cisoid or transoid farnesyl cation. The 10,1 cyclization reaction from cisoid and transoid farnesyl cation was monitored by production of α-ylangene (6) and sibirene, (2), respectively. Only aromatic amino acids can be substituted. As the effect of electric stabilization reduces, the enzyme tends to synthesize more sesquiterpene from 10,1 cyclization reaction from cisoid farnesyl cation. In 5-epi-aristolochene, the residue is predicted to be involved in neutral intermediate germacrene A formation and reprotonation. Starks et al. (1997) *Science* 277:1815-1820. Since the formation of 2 is required first germacrene D formation and reprotonation. The Y566 residue may play very important role in general acid and base catalysis.

Figure 7A:
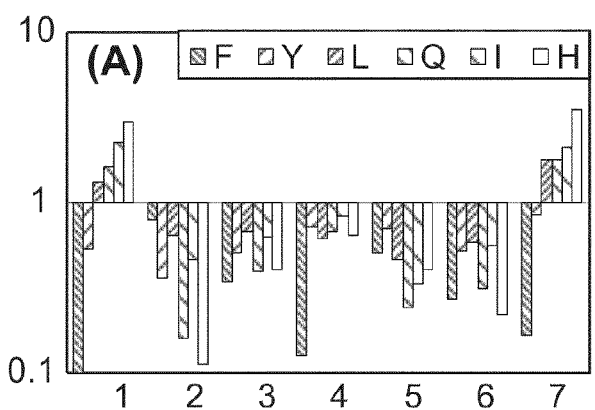
FIGS. 7A-C depict systematic plasticity residue remodeling to design β-bisabolene cyclase.
Figure 7B:
Figure 7C:
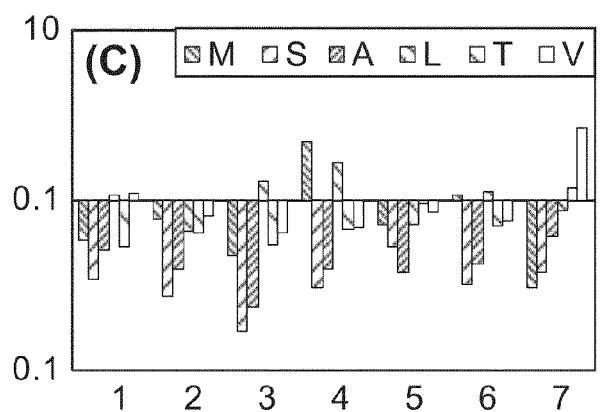

The productivity of each mutant was normalized to that of the wild-type enzyme and profiled (FIG. 7A-C; and FIGS. 8A-D). Although many of these residues were identified to be plastic, four residues significantly affected the catalysis: W315, M447, S484, and Y566.

FIGS. 7A-C; and FIGS. 8A-D. Systematic plasticity residue remodeling to design β-bisabolene cyclase. Chromatograms (WT), (M447H), (A336V/M447H), and (A336V/M447H/I562T) show the analysis of in vivo terpene production for wild type, M447H, A336V/M447H, and A336V/M447H/I562T, respectively. (FIG. 7A), (FIG. 7B), and (FIG. 7C) are the product profiles for each successive change to residues M447, A336, and I562 compared to that of wild type, respectively. The mutations were added to reduce the ω value (see methods for algorithm for systematic plasticity residue remodeling). M447H was initially selected for β-bisabolene cyclase construction. Mutations A336V and M562T were sequentially added to M447H, since they are predicted to reduce ω. β-bisabolene cyclase was successfully constructed from γ-humulene cyclase through A336V/M447H/M562T.

These results indicate that homology models built from proteins sharing only 25% identity may be sufficient to identify plasticity residues. Rynkiewicz et al. (2002) supra. Models built from much lower identity may also be sufficient, because active site residues tend to be more conserved throughout the same protein superfamilies. Gerlt et al. (2005) *Arch. Biochem. Biophys.* 433:59-70.

To further investigate how these plasticity residues contribute to molecular evolution and to formulate a design methodology for altered product selectivity, the mutations were systematically recombined based on the profiles obtained from saturation mutagenesis. The recombination was systematically carried out using an algorithm; systematic recombination of plasticity residues (for further detail, see Methods section). The algorithm is based on the assumption that plasticity residues are independent; hence the effect of a particular mutation on the reaction mechanism should be the same for the wild-type enzyme and any mutants. Thus, the particular mutations introduced into a gene were determined based on how much the a value (the root mean square deviation from predicted to desired functions) was reduced by combinations of possible mutations. For example, in the construction of a β-bisabolene (7) cyclase (BBA), M447H(ω=17.0; WT for 25.9), was selected initially (FIGS. 7A-C; and FIGS. 8A-D). In the second round, A336V was predicted to minimize ω most significantly (FIG. 7B, ω=8.45). A336V/M447H reduced the production of 3, 4 and 5 arising from the 11,1 cyclization reaction (chromatogram A336V/M447H). Finally, both I562T (ω=5.9) and I562V (ω=3.8) were considered (chromatogram A336V/M447H). M447H/A336V/I562T reduced 1 production and showed better selectivity for production of 7 (chromatogram A336V/M447H/I562T); thus a β-bisabolene cyclase was successfully constructed while maintaining its activity (Table 2).

TABLE 2

| Clones[*1] | Mutations[*1] | Product Distributions (%) | | | | | | | | Yield[*2] (times) | $k_{cat}$ ($s^{-1}$) | $K_m$ (μM) | $k_{cat}/K_m$ ($M^{-1}s^{-1}$) |
|---|---|---|---|---|---|---|---|---|---|---|---|---|---|
| | | 1 | 2 | 3 | 4 | 5 | 6 | 7 | 8 | | | | |
| WT | none | 1.8 | 28.2 | 33.1 | 16.0 | 5.4 | 3.9 | 11.6 | ND | 1 | $2.36 \times 10^{-2}$ | 4.66 | $5.07 \times 10^3$ |
| BFN | W315P | 45.6 | 2.8 | 2.2 | ND | ND | ND | 8.7 | 40.7 | 2.1 | $1.94 \times 10^{-3}$ | 0.179 | $1.08 \times 10^4$ |
| SIB | F312Q, M339A, M447F | 4.3 | 78.6 | 11.1 | 1.8 | 0 | 1.4 | 2.8 | ND | 1.8 | $4.63 \times 10^{-4}$ | 3.01 | $1.54 \times 10^2$ |
| HUM | M339N, S484C, M565I | 3.6 | 0.9 | 71.8 | 5.2 | 4.6 | 7.7 | 6.2 | ND | 1.2 | $1.81 \times 10^{-3}$ | 2.08 | $8.70 \times 10^2$ |
| LFN | A317N[*3], *A336S, S484C, I562V* | 1.2 | 1.0 | 9.4 | 67.0 | 11.1 | 2.2 | 8.1 | ND | 4.4 | $6.96 \times 10^{-2}$ | 3.83 | $1.81 \times 10^4$ |
| ALP | A336C, T445C, S484C, I562L, M565L | 5.6 | 0.4 | 9.1 | 15.6 | 58.8 | 2.4 | 8.1 | ND | 13 | $3.81 \times 10^{-3}$ | 4.59 | $8.31 \times 10^2$ |
| AYG | S484A, Y566F | 2.4 | 0.5 | 50.4 | 3.8 | 13.5 | 18.0 | 11.4 | ND | 3.3 | $1.21 \times 10^{-2}$ | 6.05 | $1.99 \times 10^3$ |
| BBA | A336V, M447H, I562T | 6.4 | 0.4 | 3.6 | 4.6 | 1.2 | ND | 83.8 | ND | 4.2 | $2.24 \times 10^{-2}$ | 2.88 | $7.77 \times 10^3$ |

ND means "Production is not detected"
[*1] All constructs are made based on a soluble variant
WT = wild type,
BFN = E-β-farnesene synthase,
SIB = sibirene cyclase,
HUM = γ-humulene cyclase,
LFN = longifolene cyclase,
ALP = α-longipinene cyclase,
AYG = α-ylangene over producer (another γ-humulene cyclase),
BBA = E-β-bisabolene cyclase
[*2] The yield means in vivo productivity over wild type of objective compound represented as bold.
All product distributions were represented 1-8 as 100% since these products generally corresponds to more than 85%.
They are corresponding to 75% of total products in wild type.
All product distributions were determined from triplicates, and standard deviations were lower than 2%.
All kinetic values were determined from triplicates, and standard deviations were generally lower than 15% and at most 25%.
[*3] mutation A317N which occurred unexpectedly improved in vivo productivity of longifolene cyclase The above-described method was used to create an E-β-farnesene/Z,E-α-farnesene synthase (BFN:W315P), a sibirene cyclase (SIB:F312Q/M339A/M447F), a new γ-humulene cyclase (HUM:M339N/S484C/M565I), a longifolene cyclase (LFN:A336S/S484C/I562V), an α-longipinene cyclase (ALP:A336C/T445C/S484C/I562L/M565L), and another (variant) γ-humulene cyclase (AYG:S484A/Y566F) in which α-ylangene production was significantly improved. All of the designed enzymes maintained a level of specific activity comparable to the wild type precursor (FIG. 9 and Table 2).

Figure 9:
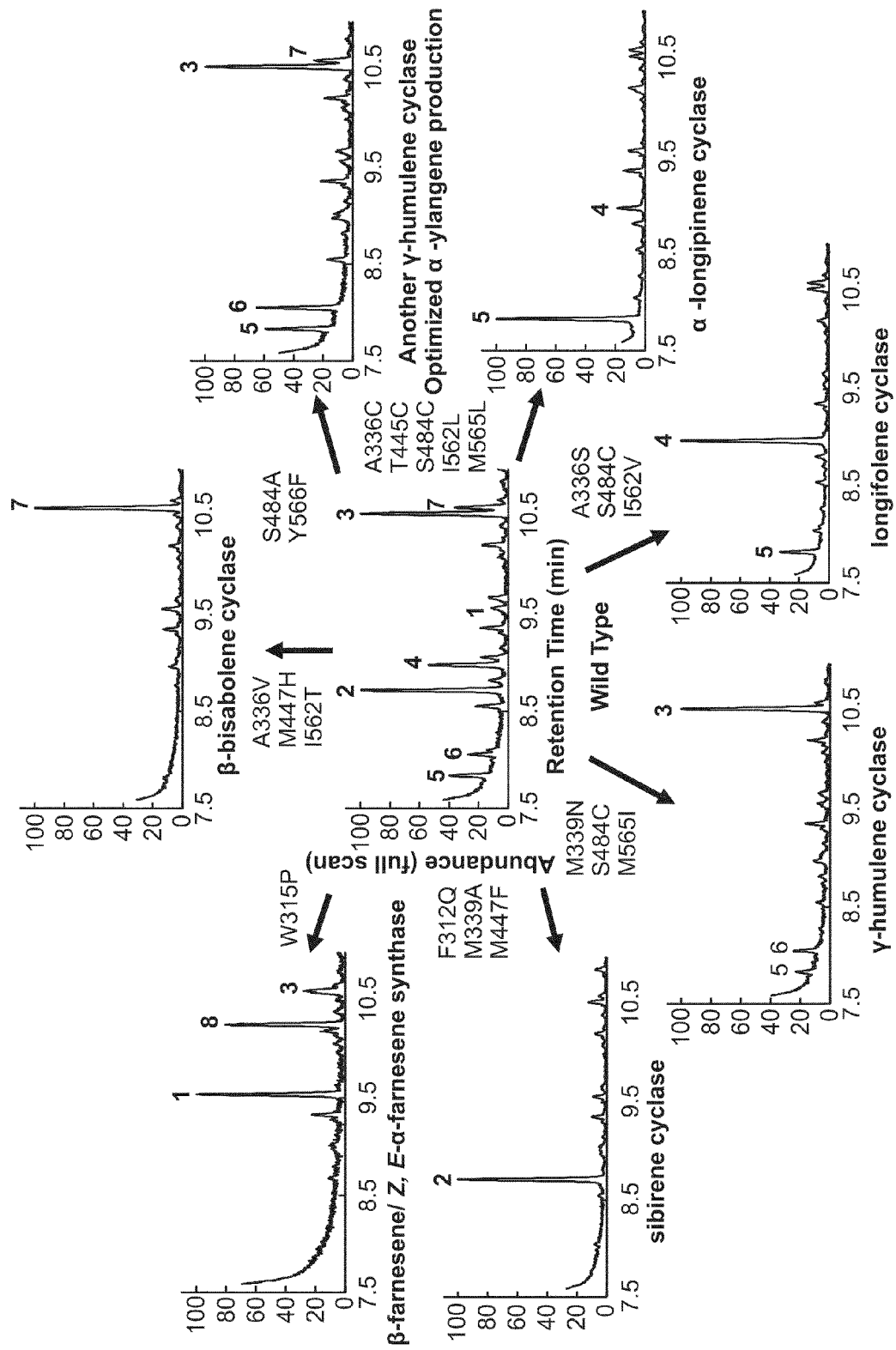
FIG. 9 depicts divergent evolution of novel sesquiterpene cyclases from γ-humulene cyclase.

FIG. 9. Divergent evolution of novel sesquiterpene cyclases from γ-humulene cyclase. Chromatograms show the GC-MS analysis for in vivo sesquiterpene production of both wild-type and variants of γ-humulene cyclase. All γ-humulene cyclase variants were designed based on the systematic plasticity residue remodeling method, and constructed by saturation mutagenesis and site directed mutagenesis. Interestingly, fewer mutations were required to shift the reaction between products arising from the same cyclization mechanism. For example, SIB to LFN requires 6 substitutions; however, ALP to LFN only requires 4 substitutions. 3, 4, and 5 all shared mutation S484C.

The codon-optimized nucleotide sequence encoding γ-humulene cyclase is depicted in FIG. 10; and the wild-type (*Abies grandis*) amino acid sequence is depicted in FIG. 11. The amino acid sequences of BBA, BFN, SIB, HUM, LFN, ALP, and AYG are depicted in FIGS. 12-18. Amino acid substitutions, compared to the amino acid sequence shown in FIG. 11, are shown as bold and underlined amino acids.

The above-described method was successfully applied in the design of product selectivity of sesquiterpene cyclases where the mutations are spatially separated (FIG. 2). The above-described method is readily adaptable to any of a variety of proteins, including, e.g., enzymes; antibodies; protein ligands of receptors, receptors; fluorescent proteins; signal proteins; small molecule binding proteins; large molecule binding proteins; and transcription factors.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A variant terpene cyclase that exhibits an altered product profile as compared to a parent terpene cyclase, wherein said variant terpene cyclase comprises an amino acid sequence selected from the group consisting of SEQ ID NOs:47-53.

2. The variant terpene cyclase of claim 1, wherein said variant terpene cyclase preferentially produces a sesquiterpene, using farnesyl diphosphate (FPP) as substrate, wherein the sesquiterpene is selected from β-bisabolene, longifolene, α-longipinene, γ-humulene, α-ylangene, sibirene, E-β-farnesene, and Z,E-α-farnesene.

* * * * *

SEQUENCE LISTING

```
<160> NUMBER OF SEQ ID NOS: 53

<210> SEQ ID NO 1
<211> LENGTH: 39
<212> TYPE: DNA
<213> ORGANISM: Artificial Sequence
<220> FEATURE:
<223> OTHER INFORMATION: synthetic primer
```

```
<220> FEATURE:
<221> NAME/KEY: misc_feature
<222> LOCATION: 19, 20, 21
<223> OTHER INFORMATION: n = A,T,C or G

<400> SEQUENCE: 1
cgtaaatgct atgtggaann ntacttctgg atggccgcg                              39

<210> SEQ ID NO 2
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 2
cgcggccatc cagaagtann nttccacata gcatttacg                              39

<210> SEQ ID NO 3
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 3
tatgtggaat tttacttcnn natggccgcg gcaatttca                              39

<210> SEQ ID NO 4
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 4
tgaaattgcc gcggccatnn ngaagtaaaa ttccacata                              39

<210> SEQ ID NO 5
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 5
gtggcattca ctaaaattnn natcttgatg acaatgtta                              39

<210> SEQ ID NO 6
<211> LENGTH: 39
<212> TYPE: DNA
<213> ORGANISM: Artificial Sequence
<220> FEATURE:
```

<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 6
taacattgtc atcaagatnn naattttagt gaatgccac                              39

<210> SEQ ID NO 7
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 7
actaaaattg cgatcttgnn nacaatgtta gatgactta                              39

<210> SEQ ID NO 8
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 8
taagtcatct aacattgtnn ncaagatcgc aattttagt                              39

<210> SEQ ID NO 9
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 9
aaaattgcga tcttgatgnn natgttagat gacttatac                              39

<210> SEQ ID NO 10
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 10
gtataagtca tctaacatnn ncatcaagat cgcaatttt                              39

<210> SEQ ID NO 11
<211> LENGTH: 39
<212> TYPE: DNA
<213> ORGANISM: Artificial Sequence

```
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 11
gaacgctatc tggaagcgnn nttgcaggat gccgaatgg                                    39

<210> SEQ ID NO 12
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 12
ccattcggca tcctgcaann ncgcttccag atagcgttc                                    39

<210> SEQ ID NO 13
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 13
aacaatggca cccccaacnn nggtatgtgt gtacttaat                                    39

<210> SEQ ID NO 14
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 14
attaagtaca cacataccnn ngttgggggt gccattgtt                                    39

<210> SEQ ID NO 15
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 15
aatggcaccc ccaacaccnn natgtgtgta cttaatctg                                    39

<210> SEQ ID NO 16
<211> LENGTH: 39
<212> TYPE: DNA
```

<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 16
cagattaagt acacacatnn nggtgttggg ggtgccatt         39

<210> SEQ ID NO 17
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 17 ggcacccca acaccggtnn ntgtgtactt aatctgatc          39

<210> SEQ ID NO 18
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 18
gatcagatta agtacacann naccggtgtt gggggtgcc         39

<210> SEQ ID NO 19
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 19
aacaccggta tgtgtgtann naatctgatc ccgttgctg         39

<210> SEQ ID NO 20
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 20
cagcaacggg atcagattnn ntacacacat accggtgtt         39

<210> SEQ ID NO 21
<211> LENGTH: 39

```
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 21
catctgattg aactggctnn ncgactggtc gatgatgcg                                39

<210> SEQ ID NO 22
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 22
cgcatcatcg accagtcgnn nagccagttc aatcagatg                                39

<210> SEQ ID NO 23
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 23
gaactggcta gccgactgnn ngatgatgcg agagatttt                                39

<210> SEQ ID NO 24
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 24
aaaatctctc gcatcatcnn ncagtcggct agccagttc                                39

<210> SEQ ID NO 25
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 25
aaatactcat tccacgtcnn ngcgcggtcg attcagttt                                39

<210> SEQ ID NO 26
```

```
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 26
aaactgaatc gaccgcgcnn ngacgtggaa tgagtattt                                    39

<210> SEQ ID NO 27
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 27
cacgtcctgg cgcggtcgnn ncagtttatg tataaccag                                    39

<210> SEQ ID NO 28
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 28
ctggttatac ataaactgnn ncgaccgcgc caggacgtg                                    39

<210> SEQ ID NO 29
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 29
gcgcggtcga ttcagtttnn ntataaccag ggggacggg                                    39

<210> SEQ ID NO 30
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 30
cccgtccccc tggttatann naaactgaat cgaccgcgc                                    39
```

```
<210> SEQ ID NO 31
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 31
cggtcgattc agtttatgnn naaccagggg gacgggttt                              39

<210> SEQ ID NO 32
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 32
aaacccgtcc ccctggttnn ncataaactg aatcgaccg                              39

<210> SEQ ID NO 33
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 33
tttatgtata accagggnn ngggttttcg atttcgaac                               39

<210> SEQ ID NO 34
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 34
gttcgaaatc gaaaacccnn nccctggtt atacataaa                               39

<210> SEQ ID NO 35
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 35
tataaccagg gggacgggnn ntcgatttcg aacaaagtt                              39
```

<210> SEQ ID NO 36
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 36
aactttgttc gaaatcgann ncccgtcccc ctggttata            39

<210> SEQ ID NO 37
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 37
aaccaggggg acgggtttnn natttcgaac aaagttatt            39

<210> SEQ ID NO 38
<211> LENGTH: 39
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 19, 20, 21
<223> OTHER INFORMATION: n = A,T,C or G

<400> SEQUENCE: 38
aataactttg ttcgaaatnn naaacccgtc ccctggtt             39

<210> SEQ ID NO 39
<211> LENGTH: 39
<212> TYPE: DNA
<213> ORGANISM: Artificial Sequence
<220> FEATURE:
<223> OTHER INFORMATION: synthetic primer

<400> SEQUENCE: 39
gcgcggtcga ttcagtttvt ttataaccag ggggacggg            39

<210> SEQ ID NO 40
<211> LENGTH: 39
<212> TYPE: DNA
<213> ORGANISM: Artificial Sequence
<220> FEATURE:
<223> OTHER INFORMATION: synthetic primer

<400> SEQUENCE: 40
cccgtccccc tggttataaa baaactgaat cgaccgcgc            39

<210> SEQ ID NO 41
<211> LENGTH: 39
<212> TYPE: DNA
<213> ORGANISM: Artificial Sequence
<220> FEATURE:
<223> OTHER INFORMATION: synthetic primer

<400> SEQUENCE: 41
gtggcattca ctaaaatttg catcttgatg acaatgtta                                39

<210> SEQ ID NO 42
<211> LENGTH: 39
<212> TYPE: DNA
<213> ORGANISM: Artificial Sequence
<220> FEATURE:
<223> OTHER INFORMATION: synthetic primer

<400> SEQUENCE: 42
taacattgtc atcaagatgc aaattttagt gaatgccac                                39

<210> SEQ ID NO 43
<211> LENGTH: 45
<212> TYPE: DNA
<213> ORGANISM: Artificial Sequence
<220> FEATURE:
<223> OTHER INFORMATION: synthetic primer

<400> SEQUENCE: 43
ctgaacaatg gcaccccccaa ctgcggtatg tgtgtactta atctg                        45

<210> SEQ ID NO 44
<211> LENGTH: 45
<212> TYPE: DNA
<213> ORGANISM: Artificial Sequence
<220> FEATURE:
<223> OTHER INFORMATION: synthetic primer

<400> SEQUENCE: 44
cagattaagt acacacatac cgcagttggg ggtgccattg ttcag                         45

<210> SEQ ID NO 45
<211> LENGTH: 1782
<212> TYPE: DNA
<213> ORGANISM: Artificial Sequence
<220> FEATURE:
<223> OTHER INFORMATION: Codon-optimized sequence encoding
      gamma-humulene cyclase

<400> SEQUENCE: 45
atggctcaaa tcagcgaatc agtgtctcca agcaccgacc ttaaaagcac ggaatcttct         60
attaccagca accgcacgg taacatgtgg aagatgacc gcattcagag cttaaacagc          120
ccatatggcg cacccgctta tcaggaacgt agcgaaaaat tgattgaaga aattaagctc        180
ctgtttctgt ccgatatgga cgatagttgc aatgattcgg atcgcgactt gatcaaacgc        240
ctggagatcg tagatacggt tgagtgtctg gcattgatc gtcatttcca acctgaaatt        300
aagctggcgc tggattacgt gtaccgttgc tggaatgagc gtggcatcgg agaaggtagc        360
cgtgatagct aaaaaagga cctgaatgcg accgccttgg gctttcgggc tttacgctta        420
caccgttata atgtaagctc aggagtgctg gagaacttcc gtgatgacaa tggtcaattc       480
ttttgcggtt ctactgtgga ggaggaaggc gcggaggcct acaataaaca tgtacgttgc       540
atgctgtccc tgtcccgcgc ttccaatatt ttattcccgg gcgagaaagt gatggaagaa       600
gcgaaggcgt ttacgaccaa ctatcttaag aaagtcctgg cgggtcgtga agcaactcat       660
gtcgacgaga gtctccttgg agaggtcaag tatgcactag aatttccgtg gcattgttcc       720
gtgcagcgct gggaggcacg ttcttttatc gaaattttcg gtcagattga tagtgaactg       780
aaaagcaacc tctctaaaaa aatgctcgaa ctcgcaaaac ttgattttaa catactccag       840

-continued

```
tgtacgcatc aaaaagagct ccagatcatt agtcgatggt tcgccgattc aagtatcgca    900
agtctgaact tttaccgtaa atgctatgtg aatttttact tctggatggc cgcggcaatt    960
tcagaaccag aatttagtgg ctctcgcgtg gcattcacta aaattgcgat cttgatgaca   1020
atgttagatg acttatacga cacgcatggg acgctggatc aattgaaaat atttaccgaa   1080
ggtgtgcgca ggtgggacgt gtcgctggtg gagggcctgc cggatttcat gaaaattgcc   1140
tttgagttct ggttaaagac ctccaacgaa ctgattgcgg aggcggttaa ggcccaaggc   1200
caggatatgg cggcctatat ccgcaaaaac gcttgggaac gctatctgga agcgtatttg   1260
caggatgccg aatggatcgc caccggtcac gttccgacat cgatgaata tctgaacaat   1320
ggcacccca acaccggtat gtgtgtactt aatctgatcc cgttgctgct tatgggcgaa   1380
cacttgccga tcgatattct tgaacagatc tttctgccga gccggttcca ccatctgatt   1440
gaactggcta gccgactggt cgatgatgcg agagattttc aagccgaaaa agatcatggt   1500
gatttatcct gcatcgaatg ctacctgaaa gaccatccgg aatcaacagt tgaagacgcc   1560
ctgaatcacg tcaacggcct gctggggaat tgtttgctgg aaatgaattg gaaatttctg   1620
aaaaaacagg actcggtacc tctgtcgtgt aaaaaatact cattccacgt cctggcgcgg   1680
tcgattcagt ttatgtataa ccaggggac gggttttcga tttcgaacaa agttattaaa   1740
gaccaggtcc agaaagttct aatcgttccg gttcctatat aa                      1782
```

<210> SEQ ID NO 46
<211> LENGTH: 593
<212> TYPE: PRT
<213> ORGANISM: Abies grandis

<400> SEQUENCE: 46

```
Met Ala Gln Ile Ser Glu Ser Val Pro Ser Thr Asp Leu Lys Ser
  1               5                  10                  15

Thr Glu Ser Ser Ile Thr Ser Asn Arg His Gly Asn Met Trp Glu Asp
             20                  25                  30

Asp Arg Ile Gln Ser Leu Asn Ser Pro Tyr Gly Ala Pro Ala Tyr Gln
         35                  40                  45

Glu Arg Ser Glu Lys Leu Ile Glu Glu Ile Lys Leu Leu Phe Leu Ser
     50                  55                  60

Asp Met Asp Asp Ser Cys Asn Asp Ser Asp Arg Asp Leu Ile Lys Arg
 65                  70                  75                  80

Leu Glu Ile Val Asp Thr Val Glu Cys Leu Gly Ile Asp Arg His Phe
                 85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205
```

```
Leu Lys Lys Val Leu Ala Gly Arg Glu Ala Thr His Val Asp Glu Ser
    210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
        275                 280                 285
Ile Ile Ser Arg Trp Phe Ala Asp Ser Ser Ile Ala Ser Leu Asn Phe
    290                 295                 300
Tyr Arg Lys Cys Tyr Val Glu Phe Tyr Phe Trp Met Ala Ala Ala Ile
305                 310                 315                 320
Ser Glu Pro Glu Phe Ser Gly Ser Arg Val Ala Phe Thr Lys Ile Ala
                325                 330                 335
Ile Leu Met Thr Met Leu Asp Asp Leu Tyr Asp Thr His Gly Thr Leu
            340                 345                 350
Asp Gln Leu Lys Ile Phe Thr Glu Gly Val Arg Arg Trp Asp Val Ser
        355                 360                 365
Leu Val Glu Gly Leu Pro Asp Phe Met Lys Ile Ala Phe Glu Phe Trp
    370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
                405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
        435                 440                 445
Val Leu Asn Leu Ile Pro Leu Leu Leu Met Gly Glu His Leu Pro Ile
    450                 455                 460
Asp Ile Leu Glu Gln Ile Phe Leu Pro Ser Arg Phe His His Leu Ile
465                 470                 475                 480
Glu Leu Ala Ser Arg Leu Val Asp Asp Ala Arg Asp Phe Gln Ala Glu
                485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
        515                 520                 525
Gly Asn Cys Leu Leu Glu Met Asn Trp Lys Phe Leu Lys Lys Gln Asp
    530                 535                 540
Ser Val Pro Leu Ser Cys Lys Lys Tyr Ser Phe His Val Leu Ala Arg
545                 550                 555                 560
Ser Ile Gln Phe Met Tyr Asn Gln Gly Asp Gly Phe Ser Ile Ser Asn
                565                 570                 575
Lys Val Ile Lys Asp Gln Val Gln Lys Val Leu Ile Val Pro Val Pro
            580                 585                 590
Ile

<210> SEQ ID NO 47
<211> LENGTH: 593
<212> TYPE: PRT
```

<213> ORGANISM: Artificial Sequence
<220> FEATURE:
<223> OTHER INFORMATION: E-beta-bisabolene synthase

<400> SEQUENCE: 47

```
Met Ala Gln Ile Ser Glu Ser Val Ser Pro Thr Asp Leu Lys Ser
 1               5                  10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
            35                  40                  45

Glu Arg Ser Glu Lys Leu Ile Glu Glu Ile Lys Leu Leu Phe Leu Ser
 50                  55                  60

Asp Met Asp Asp Ser Cys Asn Asp Ser Asp Arg Asp Leu Ile Lys Arg
 65                  70                  75                  80

Leu Glu Ile Val Asp Thr Val Glu Cys Leu Gly Ile Asp Arg His Phe
                 85                  90                  95

Gln Pro Glu Ile Lys Leu Ala Leu Asp Tyr Val Tyr Arg Cys Trp Asn
                100                 105                 110

Glu Arg Gly Ile Gly Glu Gly Ser Arg Asp Ser Leu Lys Lys Asp Leu
            115                 120                 125

Asn Ala Thr Ala Leu Gly Phe Arg Ala Leu Arg Leu His Arg Tyr Asn
130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
            195                 200                 205

Leu Lys Lys Val Leu Ala Gly Arg Glu Ala Thr His Val Asp Glu Ser
210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
            275                 280                 285

Ile Ile Ser Arg Trp Phe Ala Asp Ser Ser Ile Ala Ser Leu Asn Phe
290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Val
                325                 330                 335

Ile Leu Met Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
            355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
```

```
                385                 390                 395                 400
Gln Asp Met Ala Ala Tyr Ile Arg Lys Asn Ala Trp Glu Arg Tyr Leu
                    405                 410                 415
Glu Ala Tyr Leu Gln Asp Ala Glu Trp Ile Ala Thr Gly His Val Pro
                420                 425                 430
Thr Phe Asp Glu Tyr Leu Asn Asn Gly Thr Pro Asn Thr Gly His Cys
            435                 440                 445
Val Leu Asn Leu Ile Pro Leu Leu Met Gly Glu His Leu Pro Ile
    450                 455                 460
Asp Ile Leu Glu Gln Ile Phe Leu Pro Ser Arg Phe His His Leu Ile
465                 470                 475                 480
Glu Leu Ala Ser Arg Leu Val Asp Asp Ala Arg Asp Phe Gln Ala Glu
                485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
            515                 520                 525
Gly Asn Cys Leu Leu Glu Met Asn Trp Lys Phe Leu Lys Lys Gln Asp
    530                 535                 540
Ser Val Pro Leu Ser Cys Lys Lys Tyr Ser Phe His Val Leu Ala Arg
545                 550                 555                 560
Ser Thr Gln Phe Met Tyr Asn Gln Gly Asp Gly Phe Ser Ile Ser Asn
                565                 570                 575
Lys Val Ile Lys Asp Gln Val Gln Lys Val Leu Ile Val Pro Val Pro
            580                 585                 590
Ile

<210> SEQ ID NO 48
<211> LENGTH: 593
<212> TYPE: PRT
<213> ORGANISM: Artificial Sequence
<220> FEATURE:
<223> OTHER INFORMATION: E-beta-farnesene/Z,E-alpha-farnesene synthase

<400> SEQUENCE: 48

Met Ala Gln Ile Ser Glu Ser Val Ser Pro Ser Thr Asp Leu Lys Ser
1               5                   10                  15
Thr Glu Ser Ser Ile Thr Ser Asn Arg His Gly Asn Met Trp Glu Asp
                20                  25                  30
Asp Arg Ile Gln Ser Leu Asn Ser Pro Tyr Gly Ala Pro Ala Tyr Gln
            35                  40                  45
Glu Arg Ser Glu Lys Leu Ile Glu Glu Ile Lys Leu Leu Phe Leu Ser
        50                  55                  60
Asp Met Asp Asp Ser Cys Asn Asp Ser Asp Arg Asp Leu Ile Lys Arg
65                  70                  75                  80
Leu Glu Ile Val Asp Thr Val Glu Cys Leu Gly Ile Asp Arg His Phe
                85                  90                  95
Gln Pro Glu Ile Lys Leu Ala Leu Asp Tyr Val Tyr Arg Cys Trp Asn
            100                 105                 110
Glu Arg Gly Ile Gly Glu Gly Ser Arg Asp Ser Leu Lys Lys Asp Leu
        115                 120                 125
Asn Ala Thr Ala Leu Gly Phe Arg Ala Leu Arg Leu His Arg Tyr Asn
    130                 135                 140
Val Ser Ser Gly Val Leu Glu Asn Phe Arg Asp Asp Asn Gly Gln Phe
145                 150                 155                 160
```

-continued

```
Phe Cys Gly Ser Thr Val Glu Glu Gly Ala Glu Ala Tyr Asn Lys
                165                 170                 175
His Val Arg Cys Met Leu Ser Leu Ser Arg Ala Ser Asn Ile Leu Phe
            180                 185                 190
Pro Gly Glu Lys Val Met Glu Ala Lys Ala Phe Thr Thr Asn Tyr
        195                 200                 205
Leu Lys Lys Val Leu Ala Gly Arg Glu Ala Thr His Val Asp Glu Ser
    210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                245                 250                 255
Asp Ser Glu Leu Lys Ser Asn Leu Ser Lys Lys Met Leu Glu Leu Ala
                260                 265                 270
Lys Leu Asp Phe Asn Ile Leu Gln Cys Thr His Gln Lys Glu Leu Gln
            275                 280                 285
Ile Ile Ser Arg Trp Phe Ala Asp Ser Ser Ile Ala Ser Leu Asn Phe
    290                 295                 300
Tyr Arg Lys Cys Tyr Val Glu Phe Tyr Pro Met Ala Ala Ala Ile
305                 310                 315                 320
Ser Glu Pro Glu Phe Ser Gly Ser Arg Val Ala Phe Thr Lys Ile Ala
                325                 330                 335
Ile Leu Met Thr Met Leu Asp Asp Leu Tyr Asp Thr His Gly Thr Leu
                340                 345                 350
Asp Gln Leu Lys Ile Phe Thr Glu Gly Val Arg Arg Trp Asp Val Ser
            355                 360                 365
Leu Val Glu Gly Leu Pro Asp Phe Met Lys Ile Ala Phe Glu Phe Trp
    370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
                405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
        435                 440                 445
Val Leu Asn Leu Ile Pro Leu Leu Leu Met Gly Glu His Leu Pro Ile
    450                 455                 460
Asp Ile Leu Glu Gln Ile Phe Leu Pro Ser Arg Phe His His Leu Ile
465                 470                 475                 480
Glu Leu Ala Ser Arg Leu Val Asp Asp Ala Arg Asp Phe Gln Ala Glu
                485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
        515                 520                 525
Gly Asn Cys Leu Leu Glu Met Asn Trp Lys Phe Leu Lys Lys Gln Asp
    530                 535                 540
Ser Val Pro Leu Ser Cys Lys Lys Tyr Ser Phe His Val Leu Ala Arg
545                 550                 555                 560
Ser Ile Gln Phe Met Tyr Asn Gln Gly Asp Gly Phe Ser Ile Ser Asn
                565                 570                 575
```

Lys Val Ile Lys Asp Gln Val Gln Lys Val Leu Ile Val Pro Val Pro
            580                 585                 590

Ile

<210> SEQ ID NO 49
<211> LENGTH: 593
<212> TYPE: PRT
<213> ORGANISM: Artificial Sequence
<220> FEATURE:
<223> OTHER INFORMATION: Sibirene cyclase

<400> SEQUENCE: 49

Met Ala Gln Ile Ser Glu Ser Val Ser Pro Ser Thr Asp Leu Lys Ser
 1               5                  10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
        275                 280                 285

Ile Ile Ser Arg Trp Phe Ala Asp Ser Ser Ile Ala Ser Leu Asn Phe
    290                 295                 300

Tyr Arg Lys Cys Tyr Val Glu Gln Tyr Phe Trp Met Ala Ala Ala Ile
305                 310                 315                 320

Ser Glu Pro Glu Phe Ser Gly Ser Arg Val Ala Phe Thr Lys Ile Ala
                325                 330                 335

Ile Leu Ala Thr Met Leu Asp Asp Leu Tyr Asp Thr His Gly Thr Leu

-continued

```
                    340             345             350
Asp Gln Leu Lys Ile Phe Thr Glu Gly Val Arg Arg Trp Asp Val Ser
            355                 360                 365

Leu Val Glu Gly Leu Pro Asp Phe Met Lys Ile Ala Phe Glu Phe Trp
    370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Phe Cys
        435                 440                 445

Val Leu Asn Leu Ile Pro Leu Leu Met Gly Glu His Leu Pro Ile
    450                 455                 460

Asp Ile Leu Glu Gln Ile Phe Leu Pro Ser Arg Phe His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525

Gly Asn Cys Leu Leu Glu Met Asn Trp Lys Phe Leu Lys Lys Gln Asp
    530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590

Ile

<210> SEQ ID NO 50
<211> LENGTH: 593
<212> TYPE: PRT
<213> ORGANISM: Artificial Sequence
<220> FEATURE:
<223> OTHER INFORMATION: gamma-humulene synthase

<400> SEQUENCE: 50

Met Ala Gln Ile Ser Glu Ser Val Ser Pro Ser Thr Asp Leu Lys Ser
1               5                   10                  15

Thr Glu Ser Ser Ile Thr Ser Asn Arg His Gly Asn Met Trp Glu Asp
            20                  25                  30

Asp Arg Ile Gln Ser Leu Asn Ser Pro Tyr Gly Ala Pro Ala Tyr Gln
        35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110
```

```
Glu Arg Gly Ile Gly Glu Gly Ser Arg Asp Ser Leu Lys Lys Asp Leu
            115                 120                 125

Asn Ala Thr Ala Leu Gly Phe Arg Ala Leu Arg Leu His Arg Tyr Asn
        130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
            195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
        275                 280                 285

Ile Ile Ser Arg Trp Phe Ala Asp Ser Ser Ile Ala Ser Leu Asn Phe
290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Ala
                325                 330                 335

Ile Leu Asn Thr Met Leu Asp Asp Leu Tyr Asp Thr His Gly Thr Leu
            340                 345                 350

Asp Gln Leu Lys Ile Phe Thr Glu Gly Val Arg Arg Trp Asp Val Ser
        355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Met Cys
        435                 440                 445

Val Leu Asn Leu Ile Pro Leu Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Cys Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525
```

```
Gly Asn Cys Leu Leu Glu Met Asn Trp Lys Phe Leu Lys Lys Gln Asp
            530                 535                 540
Ser Val Pro Leu Ser Cys Lys Lys Tyr Ser Phe His Val Leu Ala Arg
545                 550                 555                 560
Ser Ile Gln Phe Ile Tyr Asn Gln Gly Asp Gly Phe Ser Ile Ser Asn
                565                 570                 575
Lys Val Ile Lys Asp Gln Val Gln Lys Val Leu Ile Val Pro Val Pro
                580                 585                 590
Ile
```

<210> SEQ ID NO 51
<211> LENGTH: 593
<212> TYPE: PRT
<213> ORGANISM: Artificial Sequence
<220> FEATURE:
<223> OTHER INFORMATION: Longifolene cyclase

<400> SEQUENCE: 51

```
Met Ala Gln Ile Ser Glu Ser Val Ser Pro Ser Thr Asp Leu Lys Ser
  1               5                  10                  15
Thr Glu Ser Ser Ile Thr Ser Asn Arg His Gly Asn Met Trp Glu Asp
             20                  25                  30
Asp Arg Ile Gln Ser Leu Asn Ser Pro Tyr Gly Ala Pro Ala Tyr Gln
         35                  40                  45
Glu Arg Ser Glu Lys Leu Ile Glu Glu Ile Lys Leu Leu Phe Leu Ser
     50                  55                  60
Asp Met Asp Asp Ser Cys Asn Asp Ser Asp Arg Asp Leu Ile Lys Arg
 65                  70                  75                  80
Leu Glu Ile Val Asp Thr Val Glu Cys Leu Gly Ile Asp Arg His Phe
                 85                  90                  95
Gln Pro Glu Ile Lys Leu Ala Leu Asp Tyr Val Tyr Arg Cys Trp Asn
            100                 105                 110
Glu Arg Gly Ile Gly Glu Gly Ser Arg Asp Ser Leu Lys Lys Asp Leu
        115                 120                 125
Asn Ala Thr Ala Leu Gly Phe Arg Ala Leu Arg Leu His Arg Tyr Asn
    130                 135                 140
Val Ser Ser Gly Val Leu Glu Asn Phe Arg Asp Asp Asn Gly Gln Phe
145                 150                 155                 160
Phe Cys Gly Ser Thr Val Glu Glu Gly Ala Glu Ala Tyr Asn Lys
                165                 170                 175
His Val Arg Cys Met Leu Ser Leu Ser Arg Ala Ser Asn Ile Leu Phe
            180                 185                 190
Pro Gly Glu Lys Val Met Glu Glu Ala Lys Ala Phe Thr Thr Asn Tyr
        195                 200                 205
Leu Lys Lys Val Leu Ala Gly Arg Glu Ala Thr His Val Asp Glu Ser
    210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
                245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
        275                 280                 285
Ile Ile Ser Arg Trp Phe Ala Asp Ser Ser Ile Ala Ser Leu Asn Phe
```

```
                    290                 295                 300
Tyr Arg Lys Cys Tyr Val Glu Phe Tyr Phe Trp Met Asn Ala Ala Ile
305                 310                 315                 320

Ser Glu Pro Glu Phe Ser Gly Ser Arg Val Ala Phe Thr Lys Ile Ser
                325                 330                 335

Ile Leu Met Thr Met Leu Asp Asp Leu Tyr Asp Thr His Gly Thr Leu
                340                 345                 350

Asp Gln Leu Lys Ile Phe Thr Glu Gly Val Arg Arg Trp Asp Val Ser
                355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
                420                 425                 430

Thr Phe Asp Glu Tyr Leu Asn Asn Gly Thr Pro Asn Thr Gly Met Cys
                435                 440                 445

Val Leu Asn Leu Ile Pro Leu Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Cys Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
                500                 505                 510

Pro Glu Ser Thr Val Glu Asp Ala Leu Asn His Val Asn Gly Leu Leu
                515                 520                 525

Gly Asn Cys Leu Leu Glu Met Asn Trp Lys Phe Leu Lys Lys Gln Asp
                530                 535                 540

Ser Val Pro Leu Ser Cys Lys Lys Tyr Ser Phe His Val Leu Ala Arg
545                 550                 555                 560

Ser Val Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
                580                 585                 590

Ile

<210> SEQ ID NO 52
<211> LENGTH: 593
<212> TYPE: PRT
<213> ORGANISM: Artificial Sequence
<220> FEATURE:
<223> OTHER INFORMATION: alpha-longipinene synthase

<400> SEQUENCE: 52

Met Ala Gln Ile Ser Glu Ser Val Ser Pro Ser Thr Asp Leu Lys Ser
 1               5                  10                  15

Thr Glu Ser Ser Ile Thr Ser Asn Arg His Gly Asn Met Trp Glu Asp
                20                  25                  30

Asp Arg Ile Gln Ser Leu Asn Ser Pro Tyr Gly Ala Pro Ala Tyr Gln
                35                  40                  45

Glu Arg Ser Glu Lys Leu Ile Glu Glu Ile Lys Leu Leu Phe Leu Ser
            50                  55                  60
```

```
Asp Met Asp Asp Ser Cys Asn Asp Ser Asp Arg Asp Leu Ile Lys Arg
 65                  70                  75                  80

Leu Glu Ile Val Asp Thr Val Glu Cys Leu Gly Ile Asp Arg His Phe
                 85                  90                  95

Gln Pro Glu Ile Lys Leu Ala Leu Asp Tyr Val Tyr Arg Cys Trp Asn
                100                 105                 110

Glu Arg Gly Ile Gly Glu Gly Ser Arg Asp Ser Leu Lys Lys Asp Leu
                115                 120                 125

Asn Ala Thr Ala Leu Gly Phe Arg Ala Leu Arg Leu His Arg Tyr Asn
130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Glu Gly Ala Glu Ala Tyr Asn Lys
                165                 170                 175

His Val Arg Cys Met Leu Ser Leu Ser Arg Ala Ser Asn Ile Leu Phe
                180                 185                 190

Pro Gly Glu Lys Val Met Glu Glu Ala Lys Ala Phe Thr Thr Asn Tyr
                195                 200                 205

Leu Lys Lys Val Leu Ala Gly Arg Glu Ala Thr His Val Asp Glu Ser
210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
                260                 265                 270

Lys Leu Asp Phe Asn Ile Leu Gln Cys Thr His Gln Lys Glu Leu Gln
                275                 280                 285

Ile Ile Ser Arg Trp Phe Ala Asp Ser Ser Ile Ala Ser Leu Asn Phe
                290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Cys
                325                 330                 335

Ile Leu Met Thr Met Leu Asp Asp Leu Tyr Asp Thr His Gly Thr Leu
                340                 345                 350

Asp Gln Leu Lys Ile Phe Thr Glu Gly Val Arg Arg Trp Asp Val Ser
                355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
                420                 425                 430

Thr Phe Asp Glu Tyr Leu Asn Asn Gly Thr Pro Asn Cys Gly Met Cys
                435                 440                 445

Val Leu Asn Leu Ile Pro Leu Leu Met Gly Glu His Leu Pro Ile
                450                 455                 460

Asp Ile Leu Glu Gln Ile Phe Leu Pro Ser Arg Phe His His Leu Ile
465                 470                 475                 480
```

-continued

```
Glu Leu Ala Cys Arg Leu Val Asp Asp Ala Arg Asp Phe Gln Ala Glu
            485                 490                 495
Lys Asp His Gly Asp Leu Ser Cys Ile Glu Cys Tyr Leu Lys Asp His
        500                 505                 510
Pro Glu Ser Thr Val Glu Asp Ala Leu Asn His Val Asn Gly Leu Leu
        515                 520                 525
Gly Asn Cys Leu Leu Glu Met Asn Trp Lys Phe Leu Lys Lys Gln Asp
    530                 535                 540
Ser Val Pro Leu Ser Cys Lys Lys Tyr Ser Phe His Val Leu Ala Arg
545                 550                 555                 560
Ser Leu Gln Phe Leu Tyr Asn Gln Gly Asp Gly Phe Ser Ile Ser Asn
                565                 570                 575
Lys Val Ile Lys Asp Gln Val Gln Lys Val Leu Ile Val Pro Val Pro
            580                 585                 590
Ile

<210> SEQ ID NO 53
<211> LENGTH: 593
<212> TYPE: PRT
<213> ORGANISM: Artificial Sequence
<220> FEATURE:
<223> OTHER INFORMATION: variant gamma-humulene cyclase

<400> SEQUENCE: 53

Met Ala Gln Ile Ser Glu Ser Val Ser Pro Ser Thr Asp Leu Lys Ser
  1               5                  10                  15
Thr Glu Ser Ser Ile Thr Ser Asn Arg His Gly Asn Met Trp Glu Asp
                 20                  25                  30
Asp Arg Ile Gln Ser Leu Asn Ser Pro Tyr Gly Ala Pro Ala Tyr Gln
             35                  40                  45
Glu Arg Ser Glu Lys Leu Ile Glu Glu Ile Lys Leu Leu Phe Leu Ser
         50                  55                  60
Asp Met Asp Asp Ser Cys Asn Asp Ser Asp Arg Asp Leu Ile Lys Arg
 65                  70                  75                  80
Leu Glu Ile Val Asp Thr Val Glu Cys Leu Gly Ile Asp Arg His Phe
                 85                  90                  95
Gln Pro Glu Ile Lys Leu Ala Leu Asp Tyr Val Tyr Arg Cys Trp Asn
            100                 105                 110
Glu Arg Gly Ile Gly Glu Gly Ser Arg Asp Ser Leu Lys Lys Asp Leu
        115                 120                 125
Asn Ala Thr Ala Leu Gly Phe Arg Ala Leu Arg Leu His Arg Tyr Asn
    130                 135                 140
Val Ser Ser Gly Val Leu Glu Asn Phe Arg Asp Asp Asn Gly Gln Phe
145                 150                 155                 160
Phe Cys Gly Ser Thr Val Glu Glu Gly Ala Glu Ala Tyr Asn Lys
                165                 170                 175
His Val Arg Cys Met Leu Ser Leu Ser Arg Ala Ser Asn Ile Leu Phe
            180                 185                 190
Pro Gly Glu Lys Val Met Glu Glu Ala Lys Ala Phe Thr Thr Asn Tyr
        195                 200                 205
Leu Lys Lys Val Leu Ala Gly Arg Glu Ala Thr His Val Asp Glu Ser
    210                 215                 220
Leu Leu Gly Glu Val Lys Tyr Ala Leu Glu Phe Pro Trp His Cys Ser
225                 230                 235                 240
Val Gln Arg Trp Glu Ala Arg Ser Phe Ile Glu Ile Phe Gly Gln Ile
```

-continued

```
                    245                 250                 255
Asp Ser Glu Leu Lys Ser Asn Leu Ser Lys Lys Met Leu Glu Leu Ala
            260                 265                 270
Lys Leu Asp Phe Asn Ile Leu Gln Cys Thr His Gln Lys Glu Leu Gln
            275                 280                 285
Ile Ile Ser Arg Trp Phe Ala Asp Ser Ser Ile Ala Ser Leu Asn Phe
            290                 295                 300
Tyr Arg Lys Cys Tyr Val Glu Phe Tyr Phe Trp Met Ala Ala Ala Ile
305                 310                 315                 320
Ser Glu Pro Glu Phe Ser Gly Ser Arg Val Ala Phe Thr Lys Ile Ala
            325                 330                 335
Ile Leu Met Thr Met Leu Asp Asp Leu Tyr Asp Thr His Gly Thr Leu
            340                 345                 350
Asp Gln Leu Lys Ile Phe Thr Glu Gly Val Arg Arg Trp Asp Val Ser
            355                 360                 365
Leu Val Glu Gly Leu Pro Asp Phe Met Lys Ile Ala Phe Glu Phe Trp
            370                 375                 380
Leu Lys Thr Ser Asn Glu Leu Ile Ala Glu Ala Val Lys Ala Gln Gly
385                 390                 395                 400
Gln Asp Met Ala Ala Tyr Ile Arg Lys Asn Ala Trp Glu Arg Tyr Leu
            405                 410                 415
Glu Ala Tyr Leu Gln Asp Ala Glu Trp Ile Ala Thr Gly His Val Pro
            420                 425                 430
Thr Phe Asp Glu Tyr Leu Asn Asn Gly Thr Pro Asn Thr Gly Met Cys
            435                 440                 445
Val Leu Asn Leu Ile Pro Leu Leu Leu Met Gly Glu His Leu Pro Ile
450                 455                 460
Asp Ile Leu Glu Gln Ile Phe Leu Pro Ser Arg Phe His His Leu Ile
465                 470                 475                 480
Glu Leu Ala Ala Arg Leu Val Asp Asp Ala Arg Asp Phe Gln Ala Glu
            485                 490                 495
Lys Asp His Gly Asp Leu Ser Cys Ile Glu Cys Tyr Leu Lys Asp His
            500                 505                 510
Pro Glu Ser Thr Val Glu Asp Ala Leu Asn His Val Asn Gly Leu Leu
            515                 520                 525
Gly Asn Cys Leu Leu Glu Met Asn Trp Lys Phe Leu Lys Lys Gln Asp
530                 535                 540
Ser Val Pro Leu Ser Cys Lys Lys Tyr Ser Phe His Val Leu Ala Arg
545                 550                 555                 560
Ser Ile Gln Phe Met Phe Asn Gln Gly Asp Gly Phe Ser Ile Ser Asn
            565                 570                 575
Lys Val Ile Lys Asp Gln Val Gln Lys Val Leu Ile Val Pro Val Pro
            580                 585                 590
Ile
```